(12) United States Patent
Mosser

(10) Patent No.: US 10,596,297 B2
(45) Date of Patent: Mar. 24, 2020

(54) METHOD FOR PREPARING A FIBRILLAR COLLAGEN MATRIX

(71) Applicant: Université Pierre et Marie Curie, Paris (FR)

(72) Inventor: Gervaise Mosser, Paris (FR)

(73) Assignees: SORBONNE UNIVERSITE, Paris (FR); Centre National de la Recherche Scientifique, Paris (FR)

(*) Notice: Subject to any disclaimer, the term of this patent is extended or adjusted under 35 U.S.C. 154(b) by 192 days.

(21) Appl. No.: 15/021,667

(22) PCT Filed: Oct. 1, 2014

(86) PCT No.: PCT/IB2014/064990
§ 371 (c)(1),
(2) Date: Mar. 11, 2016

(87) PCT Pub. No.: WO2015/049646
PCT Pub. Date: Apr. 9, 2015

(65) Prior Publication Data
US 2016/0228605 A1    Aug. 11, 2016

(30) Foreign Application Priority Data

Oct. 2, 2013 (FR) .................................... 13 59555

(51) Int. Cl.
*A61L 27/24* (2006.01)
*C07K 14/78* (2006.01)

(52) U.S. Cl.
CPC .............. *A61L 27/24* (2013.01); *C07K 14/78* (2013.01); *A61L 2430/16* (2013.01)

(58) Field of Classification Search
None
See application file for complete search history.

(56) References Cited

FOREIGN PATENT DOCUMENTS

| FR | 2 944 706 A1 | 10/2010 |
| FR | 2 966 047 A1 | 4/2012 |
| WO | 2007/106812 A2 | 9/2007 |

OTHER PUBLICATIONS

Gobeaux I 2007 Langmuir 23: 6411-6417. (Year: 2007).*
Gobeaux II 2008 J Mol Biot 376: 1509-1522. (Year: 2008).*
WO 2012052679 translation, obtained from Google patents on Apr. 5, 2018: 8 pages. (Year: 2012).*
International Search Report dated Nov. 17, 2014, issued in corresponding International Application No. PCT/IB2014/064990, filed Oct. 1, 2014, 5 pages.

* cited by examiner

*Primary Examiner* — Marsha Tsay
(74) *Attorney, Agent, or Firm* — Christensen O'Connor Johnson Kindness PLLC

(57) ABSTRACT

The present invention relates to a method for preparing a fibrillar collagen matrix, which is advantageously transparent or composite, suitable for being used as a biomaterial, in particular as a corneal substitute.

14 Claims, 22 Drawing Sheets

| Condition | c(HCl) [mmol/l] | c(CH$_3$COOH) [mmol/l] | pH measured |
|---|---|---|---|
| #4 | 1.25 | 70 | |
| #6 | 0.30 | 120 | 2.86 |
| #7 | 0.30 | 220 | 2.61 |
| #8 | 0.30 | 320 | 2.57 |
| #9 | 0.60 | 36 | 2.91 |
| #10 | 0.90 | 36 | 2.85 |
| #11 | 1.25 | 36 | 2.78 |
| #12 | 0.90 | 120 | 2.69 |
| #13 | 0.90 | 220 | 2.59 |
| #14 | 0.60 | 220 | 2.60 |
| #15 | 0.60 | 120 | 2.73 |
| #20 | 1.25 | 200 | 2.67 |
| #21 | 1.25 | 300 | 2.64 |
| #22 | 1.25 | 500 | 2.53 |
| #24 | 1.25 | 800 | 2.33 |
| #24 | 1.50 | 36 | 2.53 |
| #27 | 1.50 | 120 | 2.69 |
| #30 | 1.50 | 220 | 1.50 |
| #33 | 0.30 | 36 | 0.30 |
| #34 | 1.25 | 120 | 1.25 |
| #35 | 0.3 | 5 | |
| #36 | 0.3 | 10 | |
| #37 | 0.3 | 20 | |
| #38 | 0.3 | 40 | |

|  | Procedure 1 | Procedure 2 |
|---|---|---|
| Mean T | 95.5 % | 96.0 % |
| Relative mean ΔT | 4.25 % | 0.72 % |
| Relative reduction in ΔT | 83 % ||

(A)

(B)

(A)

(B)

| Maximum tensile strength (Pa) | | | | |
|---|---|---|---|---|
| Tests | 15 mg/ml | 30 mg/ml | 60 mg/ml | 90 mg/ml |
| 1 | 5.8 E+03 | 64814 | 311627 | 208000 |
| 2 | | 74510 | 202564 | 287179 |
| 3 | | 52000 | 261538 | 280000 |
| Mean | 5.8 E+03 | 6.4 E+04 | 2.6 E+05 | 2.6 E+05 |
| SEM | 0.0 E+00 | 4.3 E+03 | 1.9 E+04 | 1.5 E+04 |

Maximum elongation at break (%)

| Tests | 15 mg/ml | 30 mg/ml | 60 mg/ml | 90 mg/ml |
|---|---|---|---|---|
| 1 | 7.0 E+01 | 93 | 96 | 45 |
| 2 |  | 105 | 70 | 57,8 |
| 3 |  | 98 | 76 | 59 |
| Mean | 7,0 E+01 | 9,9 E+01 | 8,1 E+01 | 5,4 E+01 |
| SEM | 0,0 E+00 | 2,3 E+00 | 4,8 E+00 | 2,6 E+00 |

| Transparency of matrices at 60 mg/ml of collagen as a function of physicochemical conditions ||||| 
|---|---|---|---|---|
| Condition | HCl (mM) | $CH_3COOH$ (mM) | T Mean (%) | |
| #35 | 0.3 | 5 | 90 | T max 91% |
| #36 | 0.3 | 10 | 86 | |
| #37 | 0.3 | 20 | 89 | |

Figure 20

| Transparency of matrices, collagen at 90 mg/ml (condition 36) ||
|---|---|
| | T% |
| 0.3 mM HCl<br>10 mM $CH_3COOH$ | 83 |
| | 77 |
| | 81 |
| | 79 |
| | 82 |
| | 74 |
| | 85 |
| | 79 |
| | 81 |
| Mean | 80 |
| Standard deviation | 3 |
| Confidence interval | 0.74 |
| Number of samples | 9 |
| Min value | 74 |
| Max value | 85 |

Figure 21

| Young's modulus as a function of the collagen concentration of the matrices (condition #36) | | | | |
|---|---|---|---|---|
| | in (Pa) | | in (kPa) | |
| Tests | 100 mg/ml | 111 mg/ml | 100 mg/ml | 111 mg/ml |
| 1 | 2.3 E+05 | 6.3 E+05 | 230 | 632 |
| 2 | 4.3 E+05 | 1.2 E+06 | 425 | 1181 |
| 3 | 5.6 E+05 | 7.9 E+05 | 564 | 787 |
| 4 | 2.4 E+05 | 8.9 E+05 | 241 | 889 |
| Mean | 3.7 E+05 | 8.7 E+05 | 365 | 872 |
| SEM | 8.0 E+04 | 1.2 E+05 | 80 | 116 |

| Maximum tensile strength as a function of the collagen concentration of the matrices (condition #36) | | | | |
|---|---|---|---|---|
| | in (Pa) | | in (kPa) | |
| Tests | 100 mg/ml | 111 mg/ml | 100 mg/ml | 111 mg/ml |
| 1 | 7.1 E+04 | 2.0 E+05 | 71 | 200 |
| 2 | 1.4 E+05 | 1.8 E+05 | 140 | 179 |
| 3 | 1.2 E+05 | 2.0 E+05 | 115 | 200 |
| 4 | 8.6 E+04 | 2.4 E+05 | 86 | 237 |
| Mean | 3.4 E+05 | 7.7 E+05 | 335 | 769 |
| SEM | 9.2 E+04 | 2.0 E+05 | 92 | 197 |

| Maximum elongation at break (%) | | |
|---|---|---|
| Tests | 100 mg/ml | 111 mg/ml |
| 1 | 30 | 29 |
| 2 | 42 | 15 |
| 3 | 19 | 23 |
| 4 | 27 | 25 |
| Mean | 29 | 23 |
| SEM | 4.7 | 2.9 |

Fibril diameter as a function of collagen concentration (Condition #4)

Total area analyzed per sample    12µm²

| Collagen concentration (mg/ml) | 15 | 30 | 60 | 90 |
|---|---|---|---|---|
| Mean | 27 | 12 | 12 | 14 |
| Standard deviation | 7 | 5 | 5 | 6 |
| Confidence interval | 0.21 | 0.08 | 0.06 | 0.06 |
| Number of fibrils analyzed | 552 | 2093 | 3033 | 4778 |
| Minimum diameter (nm) | 20 | 7 | 7 | 7 |
| Maximum diameter (nm) | 75 | 30 | 30 | 30 |

METHOD FOR PREPARING A FIBRILLAR COLLAGEN MATRIX

The present invention relates to a method for preparing a fibrillar collagen matrix, which is advantageously transparent or composite, capable of being used as a biomaterial, in particular as a corneal substitute.

Collagen is the most abundant protein in mammals. It is a major structural protein of connective tissues, in which it performs the role of a framework.

Indeed, the most abundant collagen types assemble in the form of fibrils, the strength of which, at equal weight, exceeds that of steel. They are combined, within supramolecular edifices, with other collagen types and also with other partner macromolecules. The network of collagen fibrils is not only responsible for the cohesion of the tissues, but also for their specific architecture which gives them particular mechanical properties. Thus, the architectural arrangement of the collagen fibrils corresponds optimally to the functions of the tissues considered according to their locations.

Collagen molecules are soluble in acid medium in vitro; collagen-based materials are obtained from acid-soluble solutions of collagen. Generally, a collagen matrix is obtained by concentrating a dilute solution of collagen according to various techniques (Wang, Y. et al., Soft Matter 2011, 7, 9659). The properties of the resulting collagen matrix can then be improved by means of additional cross-linking or compression steps.

Ratanavaraporn et al. (J Biomater Sci Polym, Ed. 2008; 19(7): 945-52) describe the effect of the type of acid used to solubilize collagen on the physical and biological properties of collagen-based materials obtained by lyophilization or crosslinking. The authors limit their study to the comparison of the effects of solubilization of collagen either with acetic acid or with hydrochloric acid.

When the collagen concentration is greater than 45-100 mg/ml, the molecules spontaneously self-assemble by virtue of their lyotropic properties and form liquid-crystal phases (N. S. Murthy, Biopolymers, 1984, 23, 1261; MM. Giraud-Guille, Biol Cell, 1989, 67, 97-101; G. Mosser et al. Matrix Biol. 2006, 25, 3-13; F. Gobeaux et al. Langmuir, 2007, 23, 6411-6417; P. De Sa Peixoto et al. Soft Matter, Vol., 7, 2011, pp. 11203-11210).

De Sa Peixoto et al. (Soft Matter, Vol., 7, 2011, pp. 11203-11210) analyze the influence of ionic strength and of the parameters of the solvent on the organization of liquid-crystal phases of collagen I. The authors evaluate in particular the phenomenon of isotropic phase/liquid crystalline phase transition of collagen in acidic solution by varying the type of acid and the concentration. The authors evaluate the effects of hydrochloric acid and acetic acid separately.

The assembly of collagen molecules with one another is conventionally referred to as "fibrillogenesis". The interactions between molecules would appear, firstly, to be provided by hydrogen bonds and electrostatic interactions. The mechanisms which generate the various collagen fibril architectures in vivo are still poorly understood and several hypotheses have been put forward. One of these hypotheses describes the creation of these assemblies as an extracellular process of self-assembly of collagen triple helices, mainly governed by conventional physicochemical forces.

In vitro, the fibrillogenesis of a collagen solution can be obtained by several techniques.

For example, it is possible to induce acid-soluble collagen fibrillogenesis by varying the pH and the ionic strength (R. L. Trelstad, et al. 1976, Proc. Natl. Acad. Sci. U.S.A., 73, 4027-4031; J. Robin Harris & Andreas Reiber, Micron, 2007, 38, 513-521) or by modulating the collagen concentration of the solution (F. Gobeaux et al., J Mol Biol, 2008, 376, 1509-1522).

The fibrillogenesis of an acid-soluble solution of collagen can therefore be induced by increasing the pH and, in the case of a concentrated solution, a sol-gel transition is then observed.

In living tissues, several types of biological macromolecule organization are encountered depending on the required mechanical properties (Hulmes et al., 2002, Journal of Structural Biology 137, 2-10). For example, a structure in the cholesteric phase is observed in compact bone and the bone trabeculae of spongy bone; this three-dimensional organization of collagen contributes to the mechanical properties of bone. It can be recreated and stabilized in vitro. Likewise, it is well known that collagen fibril organization is unidirectional in the tendons, whereas it is in the form of a plywood-like structure in the cornea.

Many techniques make it possible to obtain fibrillar collagen matrices having mechanical properties that mimic various tissues.

Thus, the inventor's laboratory is responsible for the development of techniques which make it possible to work with collagen at high concentrations and thus to take advantage of the lyotropic properties of collagen, by controlling the setting up of a supramolecular order linked to the concentration and by stabilizing this organization during a sol/gel transition so as to result in dense fibrillar matrices. These techniques have been provided in a variety of forms so as to obtain materials which each have specific properties.

Application WO 2010/004182 relates to a method for the mineralization of dense fibrillar collagen matrices for use in the bone substitute field.

Application WO 2011/151587 provides a method for obtaining dense fibrillar collagen matrices obtained at concentrations 5 to 60 times higher than the conventional hydrogels. The collagen concentration of the materials is from approximately 5 to approximately 1000 mg/ml. Depending on their concentration and their thickness, such materials are capable of being used as tissue substitute, in particular as wall reinforcement, for the manufacture of prostheses, as a soft tissue substitute or as a filling material.

Application WO 2012/052679 provides a method for obtaining transparent fibrillar matrices. The method makes it possible to promote longitudinal growth rather than transverse growth (long fibrils of small diameter) and to produce an even spacing between the fibrils. The matrices obtained according to this method are transparent.

A common limit to the techniques set out above consists of the difficulty in controlling the mechanical and optical properties of the collagen matrices.

In particular, with regard to the preparation of transparent matrices, it is known to those skilled in the art that the transparency of the material decreases when the collagen density of the material increases. It therefore remains difficult to synthesize transparent collagen matrices which have both optimal mechanical properties and optimal optical properties.

In addition, most of the techniques set out above do not make it possible to easily control the shape of the collagen matrices. There is thus a need to develop a simple method which makes it possible to mold collagen matrices while at the same time controlling their mechanical and optical properties, this being in particular in the case of transparent collagen matrices.

The present invention follows from the demonstration that the mechanical and optical properties of collagen matrices can be modulated by using collagen solutions comprising at least one strong acid and one weak acid.

The inventors have developed a method which makes it possible to obtain collagen matrices which have both mechanical characteristics and optical characteristics of great interest for the manufacture of artificial tissues or organs, in particular as a cornea substitute or as a support for cell growth. This novel method of manufacture makes it possible more particularly to synthesize fibrillar collagen matrices, the transparency of which can be modulated from entirely transparent to entirely opaque or else to synthesize composite fibrillar collagen matrices, comprising opaque zones and transparent zones.

Thus, a subject of the present invention is a method for preparing a fibrillar collagen matrix, comprising a step of fibrillogenesis of a collagen, optionally in the liquid-crystal phase, said step being carried out in a medium comprising at least one strong acid and one weak acid.

Without wishing to be bound to a particular theory, the inventors think that the presence of a combination of a strong acid and a weak acid in contact with the collagen has an effect upon the transverse growth of the fibrils and the spacing thereof during the fibrillogenesis step.

For the purposes of the present invention, the term "fibrillar collagen" is intended to mean a collagen which exhibits a non-random aggregation of collagen molecules and a period D of approximately 67 nm. For the purposes of the invention, the collagen used is a collagen which can become organized into fibrils, such as collagen type I, II, III and/or V. Advantageously, the collagen used is type I, optionally combined with other collagen types.

The notion of strong acid and of weak acid is well known to those skilled in the art. For the purposes of the invention and with reference to the studies by Brønsted-Lowry, an acid is said to be "strong" when, in an aqueous solution, it dissociates according to a virtually total reaction in water, whatever the concentration provided. The strong acids can be chosen, for example, from hydrochloric acid; sulfuric acid; perchloric acid; hydrofluoric acid; hydriodic acid; chloric acid; permanganic acid and manganic acid. An acid is said to be "weak" when, in an aqueous solution, it dissociates with water according to a reaction which is not total. The weak acids can be chosen, for example, from acetic acid, chloro-, dichloro- and trichloroacetic acid; bromoacetic acid; trifluoroacetic acid; propionic acid; ascorbic acid; valeric acid; 2-, 4- and 5-bromovaleric acid; lactic acid; citric acid; salicylic acid; acetylsalicylic acid; formic acid, acids of the uronic acid family, preferably glucuronic acid; and galacturonic acid.

In one embodiment of the invention, before fibrillogenesis, the collagen is in a liquid-crystal form (organized either in a twisted nematic phase, or in a nematic-plywood, smectic or hexagonal phase, or any other type of liquid-crystal organization) or an isotropic form.

In accordance with the invention, the fibrillar collagen matrix can be produced by taking advantage of the techniques known to those skilled in the art.

In one advantageous embodiment of the invention, the method for preparing a fibrillar collagen matrix is characterized in that it comprises the following steps:
(a) preparing an acidic aqueous solution comprising
    collagen at a concentration of between 0.1 and 10 mg/ml, advantageously of between 0.3 and 5 mg/ml, and
    at least one strong acid and one weak acid;
(b) concentrating the solution obtained in (a) to a collagen concentration of between 10 and 250 mg/ml;
(c) forming the fibrils by treating the collagen solution obtained in step (b) with a basic gas phase or with a neutral or basic liquid phase.

In accordance with the invention, the collagen solution of step (a) is obtained, by techniques known to those skilled in the art, from an initial solution of natural or recombinant collagen and solutions of strong acid and of weak acid. The collagen concentration of such a solution is between 0.1 and 10 mg/ml, advantageously between 0.3 and 5 mg/ml. The collagen solution according to step (a) has a pH of less than or equal to 4, preferably of between 2 and 4. In these solutions, the collagen is generally in the form of monomers (triple helices) and optionally in the form of nanofibrils.

Preferably, the collagen used in step (a) is a collagen in the form of monomers.

According to one embodiment of the invention, the solution of step (a) is prepared by the dialysis technique. Those skilled in the art can easily determine the dialysis parameters (type of membrane, solute concentrations of the counter-dialysis liquids) by relying in particular on the laws governing the phenomena of transport through membranes. Thus, the solution of step (a) can be obtained by dialysis of an acidic solution of collagen comprising a first acid, for example a weak acid, against a counter-dialysis solution comprising a second acid, for example a strong acid, or a mixture of strong and weak acids.

In the acidic aqueous solution of step (a),
the weak acid may be present at a concentration of between 0.1 and 500 mM, advantageously from 0.2 to 200 mM, and preferentially from 2 to 125 mM; and
the strong acid may be present at a concentration of from 0.01 to 10 mM, advantageously from 0.1 to 3 mM and preferentially from 0.2 to 2.5 mM.

Advantageously, the strong acid used is hydrochloric acid and the weak acid used is acetic acid.

In one advantageous embodiment of the invention, the acidic aqueous solution of collagen of step (a) contains acetic acid at a concentration of between 0.1 and 500 mM, preferably from 0.2 to 200 mM and preferentially from 2 to 125 mM and hydrochloric acid at a concentration of from 0.01 to 10 mM, preferably from 0.1 to 3 mM and preferentially from 0.2 to 2.5 mM.

In a manner in accordance with the invention, the step of concentrating the collagen solution (b) is carried out by techniques known to those skilled in the art.

The concentrating step can in particular be carried out by any appropriate technique using a selective membrane, for example by filtration-centrifugation, by ultrafiltration, by rapid evaporation under cryo-centrifugation or by reverse osmosis. As is known, membrane filtration techniques use selective membranes to separate molecular species according to their molecular weight. Such membranes are characterized by their separation molecular weight or by the pore size. Thus, the selective membranes used for a concentration by ultrafiltration have pores of which the size is between approximately 0.001 and 0.1 μm. The selective membranes used for a concentration by reverse osmosis are in the form of stacked membranes, which can have a very low porosity, then allowing only the solvent to pass and stopping the ions. According to one advantageous mode of the invention, the concentrating of the solution can be carried out by the filtration-centrifugation technique. To this effect, use may, for example, be made of membranes of which the separation molecular weight is 100 kDa, 50 kDa, 40 kDa, 30 kDa, 20 kDa, 10 kDa and 3 kDa. Preferentially, membranes of 30 kDa or membranes of which the size is approximately between 4 and 5 nm can be used. Those skilled in the art can easily determine the centrifugation parameters as a function of the characteristics of the concentrator and of the expected collagen concentration. The collagen concentration at the end of step (b) can be between 10 and 250 mg/ml, preferentially between 30 and 200 mg/ml, and advantageously between 40 and 120 mg/ml.

The concentrating step (b) makes it possible to have, before fibrillogenesis, a collagen in solution which is dense and advantageously in liquid-crystal form with an ordered and hierarchical organization of the collagen molecules. The obtaining of an organized liquid-crystal phase also contributes to the optimization of the mechanical and optical properties of the collagen matrices.

When a material is to be used as a tissue or organ substitute, generally the more said material mimics the tissue or organ where the implantation must take place, the better the material will implant and will allow the host's cells to appropriate it in order to regenerate a healthy tissue. Thus, mimicking a tissue or an organ means mimicking or imitating its biochemical constituents, its three-dimensional organization and its mechanical properties. The liquid-crystal phases make it possible to obtain a three-dimensional organization which mimics that found in the tissues and organs of living beings.

At the end of step (b), the collagen is therefore in a liquid-crystal form and is organized, for example, either in a twisted nematic (cholesteric) phase, or in a nematic-plywood, smectic or hexagonal phase, or any other type of liquid-crystal organization.

According to one particular embodiment of the invention, the method may also comprise, after the concentrating step (b) and before the step of forming the fibrils or fibrillogenesis step (c), a step of shaping the collagen solution. For the purposes of the present invention, the term "shaping step" is intended to mean any step during which the collagen solution obtained at the end of step (b) can in particular be placed in a mold. In one particular mode of the invention, at least two collagen solutions obtained at the end of step (b), comprising different concentrations of collagen and/or of strong acids and/or of weak acids, can be juxtaposed in the same mold. Alternatively, the collagen solutions can be shaped via successive layers. Thus, the step of shaping the collagen solution can be a molding step. In the method of the invention, the liquid-crystal organization of the collagen solutions can be maintained during the shaping step or restored after said step by means of a relaxing step. Advantageously, the liquid-crystal organization of the collagen solutions is maintained during the shaping step.

According to one particular embodiment of the invention, the method can therefore comprise a step of molding various collagen solutions obtained at the end of step (b). After the step of forming the fibrils or fibrillogenesis step (c), such a juxtaposition of collagen solutions in a mold leads to the obtaining of a matrix comprising zones of which the properties are different, in terms of collagen density, of transparency and/or of mechanical properties. This possibility can in particular be taken advantage of for the purpose of obtaining a tissue substitute comprising an area mimicking the properties of the sclera and an area mimicking the properties of the cornea. Thus, by carrying out the method according to the present invention, the inventors have been able to obtain a composite collagen matrix, comprising a central zone transparent to light and a peripheral zone opaque to light. Such a collagen matrix can be of use as a corneal substitute. In another context, this possibility can in particular be taken advantage of for the purpose of obtaining a substitute comprising a mineralized area and a non-mineralized area mimicking the properties of a bone-tendon junction.

In a manner in accordance with the invention, the fibril formation (or fibrillogenesis) in the collagen solution in step (c) is carried out by increasing the pH of the concentrated collagen solution obtained in step (b) according to techniques known to those skilled in the art. At the end of step (c), the collagen matrix has a pH of between 5 and 13.

Thus, the fibril formation (or fibrillogenesis) in the collagen solution in step (c) can be carried out by treating the collagen solution obtained in step (b) with a gas phase or a liquid.

One practical way to induce fibrillogenesis is to subject an acidic solution of collagen, which has been optionally shaped, to a gas phase consisting of ammonia vapors. The vapors, by dissolving in the solvent, induce an increase in pH of the collagen solution. Thus, according to a first embodiment, a concentrated collagen solution obtained at the end of step b), which has optionally been shaped, can be placed in a chamber containing ammonia vapor for approximately 15 hours. Another technique for fibrillogenesis of collagen solutions consists in dialyzing a small volume of acidic collagen solution against a large volume of an aqueous solution buffered at a pH of between 5 and 13. Collagen solutions which have a collagen concentration above 40 mg/ml constitute extremely viscous solutions, or even actual physical gels. Under these conditions, the concentrated collagen solutions can be made fibrillar by direct immersion in an aqueous solution with a pH of between 5 and 13 for at least 48 hours at 20° C. By way of example of an aqueous solution with a pH of between 5 and 13, mention may be made of phosphate buffered saline or ammoniacal water.

The step of fibrillogenesis using ammonia vapor makes it possible to preserve the concentration of the solution and the molecular organization put in place in the liquid phase (step (b)). This then results in a stabilized liquid-crystal phase in which the organizations put in place in the liquid phase are preserved but where the organized entity is no longer the collagen molecule, but the collagen fibril.

According to one particular embodiment of the invention, the method may also comprise a relaxing step after the step of shaping the collagen solution (b) and before the step of forming the fibrils or fibrillogenesis step (c). This period can promote the relaxation of the shear induced during the molding of the collagen solution. This step can make it possible to return to the organization of the liquid-crystal phase before molding of the collagen solution. In the case of shaping by juxtaposition of various collagen solutions in a mold, this step can promote joining between the various collagen solutions. This relaxing period can range from 12 hours to 1 week, depending on the viscosity of the solution.

According to one particular embodiment of the invention, the method may also comprise a maturing step after the step of forming the fibrils or fibrillogenesis step (c). This maturing period ranges from a few days to 2 months, depending on the ionic strength, on the temperature and on the pH. Advantageously, the maturing step lasts for from 3 days to 2 months, advantageously from 7 to 15 days. Such a maturing period can promote longitudinal growth of the fibrils and an increase in transparency.

The method of the invention makes it possible to prepare fibrillar collagen matrices of which the transparency can be modulated from entirely transparent to entirely opaque. According to one particular mode of the invention, the method also makes it possible to obtain composite fibrillar collagen matrices, comprising opaque zones and transparent zones. The method also makes it possible to obtain bespoke-molded collagen matrices. Thus, a subject of the present invention is a method for preparing a transparent fibrillar collagen matrix, comprising the following steps:

(a) preparing an acidic aqueous solution comprising:
   collagen, advantageously type I, optionally combined with other collagen types, at a concentration of between 0.1 and 10 mg/ml, advantageously of between 0.3 and 5 mg/ml, and
   at least acetic acid and hydrochloric acid;
(b) concentrating the solution obtained in (a) by filtration-centrifugation to a collagen concentration of between 10 and 250 mg/ml, advantageously between 30 and 200 mg/ml, even more advantageously between 40 and 120 mg/ml;
(c) shaping the collagen solution obtained in (b);
(d) relaxing the collagen solution at the end of step (c);
(e) forming the fibrils by treating the collagen solution obtained in step (d) with a basic gas phase;
(f) maturing the fibrils obtained in step (e) until a transparent matrix is obtained.

The collagen used in this method is a collagen which can organize into fibrils, such as collagen type I, II, III and/or V. Advantageously, the collagen used is type I, optionally combined with other collagen types.

The objective of the invention is to provide transparent, dense, fibrillar collagen matrices. For the purposes of the invention, a collagen matrix is dense when its collagen density is greater than or equal to 40 mg/ml, advantageously 90 mg/ml. For the purposes of the present invention, a transparent collagen matrix corresponds to a collagen matrix which transmits at least 80% of white light. In certain cases, a "transparent" collagen matrix or a portion of "transparent" collagen matrix corresponds to a material or a portion of material of which the transmission of white light is equivalent to that of a healthy cornea, i.e. of which the transmission of white light is at least 90% and the scattering less than 3%.

By carrying out the method according to the invention, the inventors have been able to obtain, for example, a collagen matrix of which the transparency is 97% for a collagen density of 90 mg/ml; a collagen matrix of which the transparency is 81% for a collagen density of 120 mg/ml.

The objective of the invention is also to provide composite fibrillar collagen matrices comprising opaque zones and transparent zones, i.e. at least one zone which transmits less than 80% of white light (opaque zones) and at least one transparent zone which transmits at least 80% of white light as described above.

For the purposes of the present invention, the term "stable collagen matrix" is intended to mean a matrix which does not exhibit any change in the size of the fibrils under physiological conditions (37° C., high ionic strength, etc.) and/or in the presence of cells. Thus, the matrices according to the invention do not become opaque when they are brought into contact with a medium which has a strong ionic strength, in particular a cell culture medium.

In the collagen matrices according to the invention, the collagen can be in the form of fibrils which are well individualized and relatively equidistant and organized, or in the form of aggregates of fibrils spaced out from one another by crosslinked thin fibrils which impose a relatively regular inter-distance.

The diameter of the collagen fibrils in the transparent matrices synthesized can be between 6 and 30 nm, limits included. In one advantageous embodiment of the invention, the diameter of said fibrils is 25 nm. The elementary fibrils can also become placed side by side or become grouped together in larger fibers (or fibril aggregates) which are from 0.2 to 0.5 μm in diameter (diameter of the core of the fibril aggregate) so as to give matrices which are translucent to opaque.

The fibrillar collagen matrices according to the invention can be used for many applications, including, but not limited to, clinical, therapeutic, prophylactic and cosmetic applications, and also in basic research. The collagen matrices resulting from the method according to the invention can be used as a substitute for tissues or organs of a mammal, preferably a human mammal. A subject of the invention is therefore the use of a collagen matrix for the manufacture of an artificial tissue or organ. Thus, transparent and/or composite fibrillar collagen matrices according to the invention can be used to manufacture a cornea substitute. More particularly, fibrillar collagen matrices comprising transparent zones and opaque zones, in other words composite matrices, can be used for the manufacture of cornea-sclera substitutes. Fibrillar collagen matrices comprising mineralized zones and non-mineralized zones, as described below, can be used for the manufacture of bone-tendon substitutes.

A subject of the invention is also the use of a dense, transparent, fibrillar collagen matrix or of a composite fibrillar collagen matrix for the manufacture of artificial tissues or organs, in particular as a cornea substitute, as a support for the growth of cells, in particular for the behavioral analysis thereof, or as a support for studying biomineralization processes. The collagen matrices according to the invention have low or even no cytotoxicity since they can be obtained according to a method which does not involve toxic chemical species. The collagen matrices according to the invention constitute a medium favorable to the growth of cells or of nerves.

One of the subjects of the invention relates to a cornea substitute comprising an optionally composite, preferably transparent, collagen matrix obtained according to the method of the invention.

In one particular embodiment of the invention, the collagen matrices can be used as ophthalmic implants. According to one particular mode of the invention, the collagen matrices can be biodegradable, i.e. can exhibit slow and gradual resorption. Thus, the collagen matrices according to the invention can be used as biodegradable implants for reinforcing or filling a tissue, for example an ophthalmic tissue.

The collagen matrices of the present invention can be particularly suitable for use in ophthalmic devices, in particular because they (i) can be shaped so as to form a material with an acceptable optical power, (ii) can be optically clear or transparent; (iii) constitute a medium favorable to epithelialization of the anterior surface.

According to one particular embodiment of the invention, the collagen matrix can be produced in such a way as to allow the diffusion of gases and/or of nutrients. These nutrients can include glucose and/or cell growth or differentiation factors or agents, or any molecule of interest. Such an exchange can be comparable to or greater than that of a healthy human cornea. The permeability of the material to the elements of interest can be monitored using techniques known to those skilled in the art.

The method of the invention can make it possible to prepare mineralized fibrillar collagen matrices. Thus, another subject of the invention is a method for obtaining mineralized matrices and also fibrillar collagen matrices comprising mineralized zones and non-mineralized zones.

Such matrices comprise a synthetic mineral phase, which can, for example, consist of synthetic hydroxyapatite. Matrices comprising a mineral phase can be obtained according to techniques known to those skilled in the art, in particular by precipitation of mineral-phase precursors within the collagen matrix. For the purposes of the invention, mineral-phase precursors can be calcium ions, phosphate ions such as the phosphate ion $PO_4^{3-}$, the hydrogen phosphate ion $HPO_4^{2-}$ or the dihydrogen phosphate ion $H_2PO^{4-}$, or carbonate ions such as the carbonate ion $CO_3^{2-}$ or the hydrogen carbonate ion $HCO_3^-$.

According to one particular embodiment of the invention, the method can comprise, before the concentrating step (b), a step of dialysis against an aqueous solution with a pH of between 2 and 4 comprising a weak acid and a strong acid, and mineral-phase precursors. In this embodiment of the invention, the solution comprises at least calcium ions and phosphate ions.

According to another particular embodiment of the invention, the method can comprise, after the concentrating step (b) and before the shaping step (c), a step of bringing the collagen solution (Solution 1) into contact with an aqueous solution with a pH of between 2 and 4 comprising a weak acid and a strong acid, and mineral-phase precursors (Solution 2). In this embodiment of the invention, the solution (Solution 2) comprises at least calcium ions and phosphate ions. In this embodiment, the bringing into contact of the Solutions 1 and 2 can advantageously be carried out by the filtration-centrifugation technique. An aqueous solution with a pH of between 2 and 4 comprising a weak acid and a strong acid, and mineral-phase precursors (Solution 2) is placed above the acidic collagen solution (Solution 1) obtained at the end of step b) in the same centrifugation-filtration tube. Low-speed centrifugation (4500 rpm) then makes it possible to exchange the solvent of Solution 1 with that of Solution 2 while maintaining, in Solution 1, the concentrations of strong acid, of weak acid and of collagen as obtained at the end of step b). The centrifugation also allows the collagen solution (Solution 1) to integrate the mineralization precursor ions. Advantageously, the solution containing the mineralization precursors has a concentration of phosphate precursor, for example $NaH_2PO_4$, which is below the solubility limit, preferably from 1.5 to 900 mM, more particularly from 66 to 330 mM; the concentration of calcium precursor, for example $CaCl_2$, is below the solubility limit, preferably from 2.5 mM to 1.5 M, more particularly from 10 to 550 mM. Even more advantageously, the amounts of precursors are such that the Ca/P mole ratio is between 1.5 and 1.8, preferably about 1.67. According to this embodiment of the invention, the precipitation of the mineral-phase precursors is carried out by increasing the pH of the collagen solution in which the mineral-phase precursors have diffused. Thus, the precipitation of the mineral-phase precursors can be carried out during step (c), i.e. concomitantly with the fibrillogenesis by increasing pH.

Other advantages and characteristics of the present invention may become further apparent on reading the examples below, given by way of illustration, and the appended figures:

FIG. 1 represents examples of combinations of acetic acid and hydrochloric acid concentrations used for a collagen solution at an initial concentration of 3.16 mg/ml. The table indicates the acid concentrations and the final pH of the dialysis solution. Each combination is indexed by a number which will be used in the other figures and in the remainder of the disclosure.

FIG. 2 represents the transparency (A) and the inverse of the absorption coefficient $1/\alpha_c$ (B) of the collagen matrices as a function of the physicochemical conditions listed by their index indicated in FIG. 1. The radii of the circles are proportional to the values measured. The transparency decreases as the collagen concentration increases.

FIG. 3 represents the percentage drop in the average transparency measured between 530 nm and 580 nm (along the y-axis) as a function of the collagen concentration (along the x-axis) for the conditions #9, #10 and #11. The samples obtained according to procedures 1 and 2 are respectively represented in (A) and (B).

FIG. 4 represents the mean of the transparency and the confidence intervals $2\sigma$ for 4 samples of condition #11 at 60 mg/ml prepared according to procedure 1 and 4 others according to procedure 2. The variance between the samples is significantly reduced with procedure 2.

Figure 7:
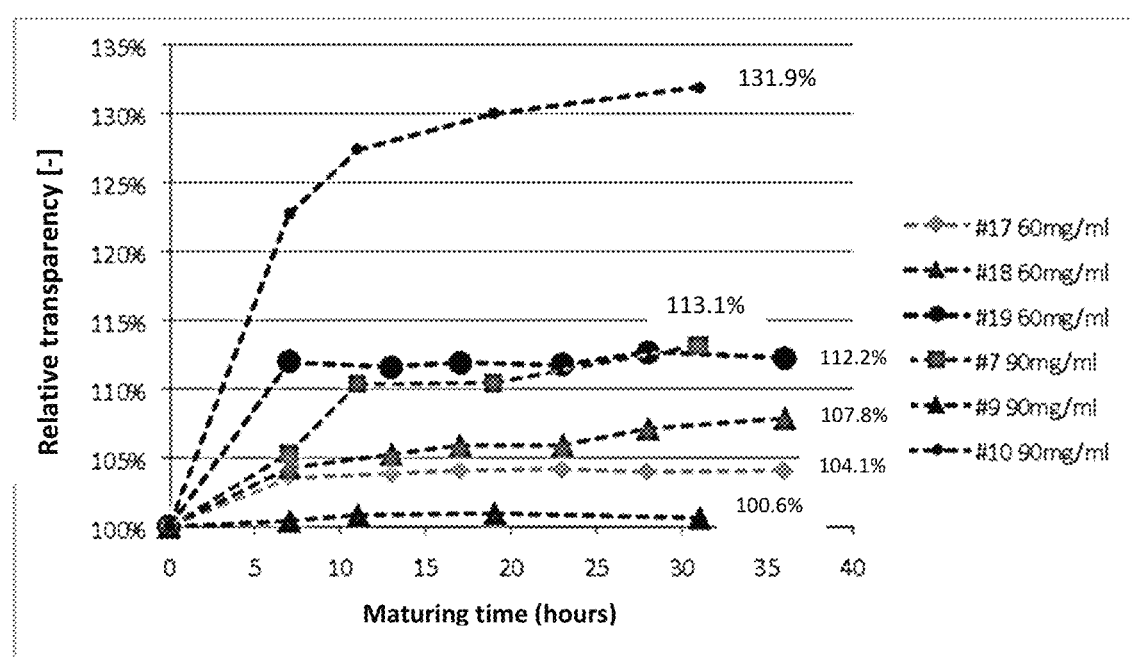

FIG. 7 represents examples of the effect of the maturation time on the samples prepared under various physicochemical and collagen-concentration conditions. The gain in transparency is strongly dependent on the two parameters. The relative transparency is represented along the y-axis and the maturation time is represented along the x-axis.

Figure 8:
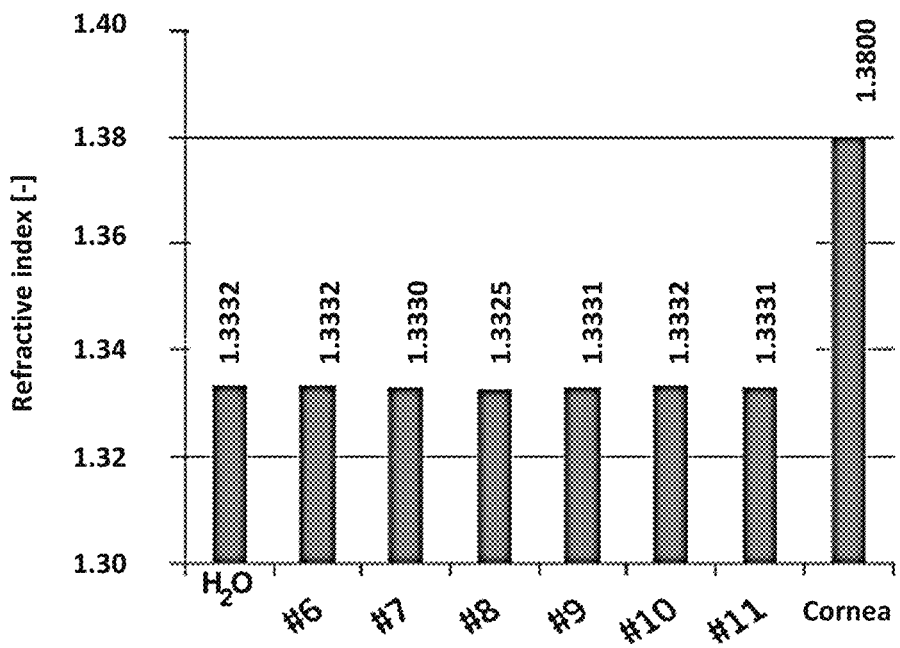
Figure 8:
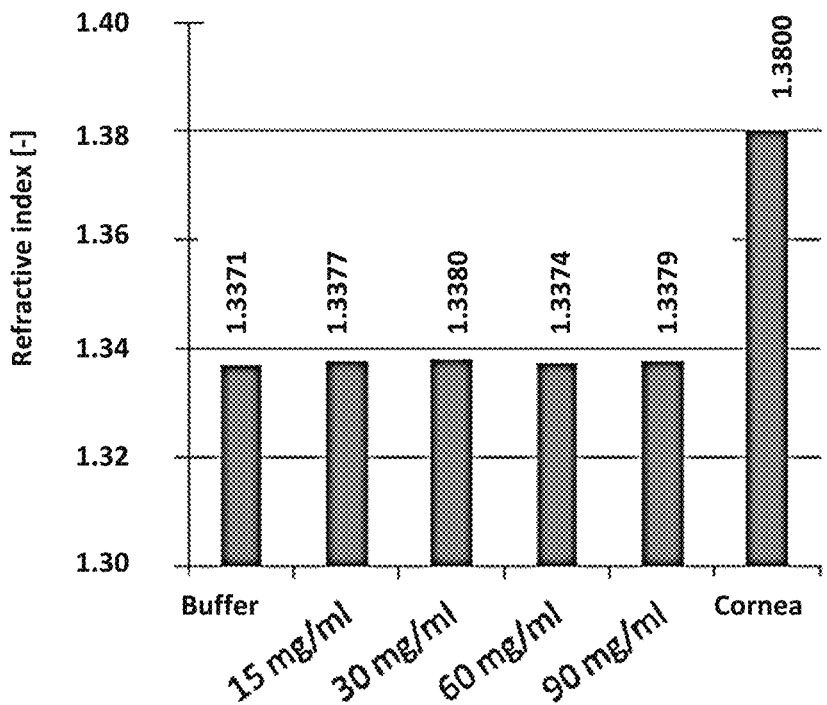

FIG. 8 represents the refractive index of collagen matrices at 584 nm; A) collagen matrices under various physiochemical conditions and at 60 mg/ml; B) collagen matrices having an epithelium reconstituted in vitro.

Figure 9:
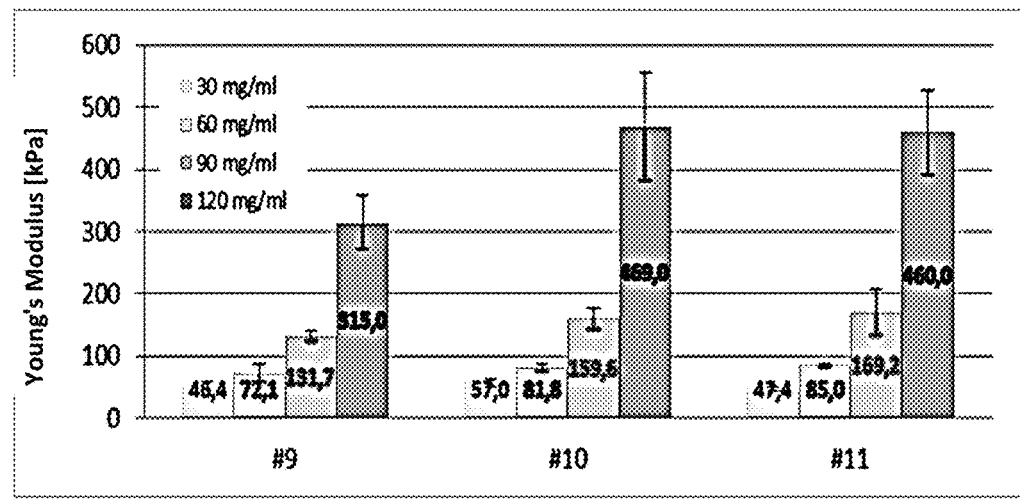
Figure 9:
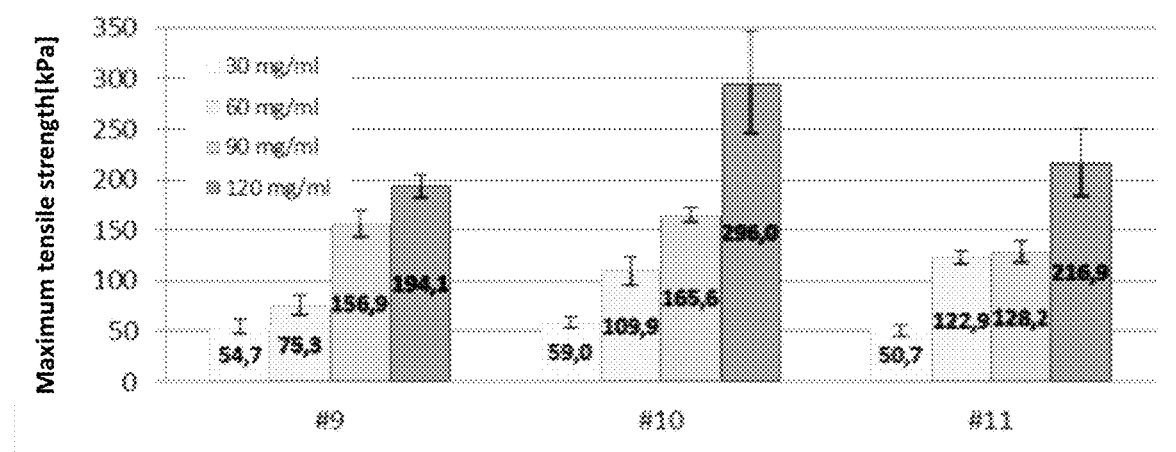

FIGS. 9(A)-(B) represent the mechanical strength of the matrices produced under conditions #9, #10 and #11 and at various concentrations; A) Young's modulus, B) Tensile strength. The Young's modulus and the maximum tensile strength increase with the collagen density. The error bars indicate the standard error of the mean.

Figure 10:
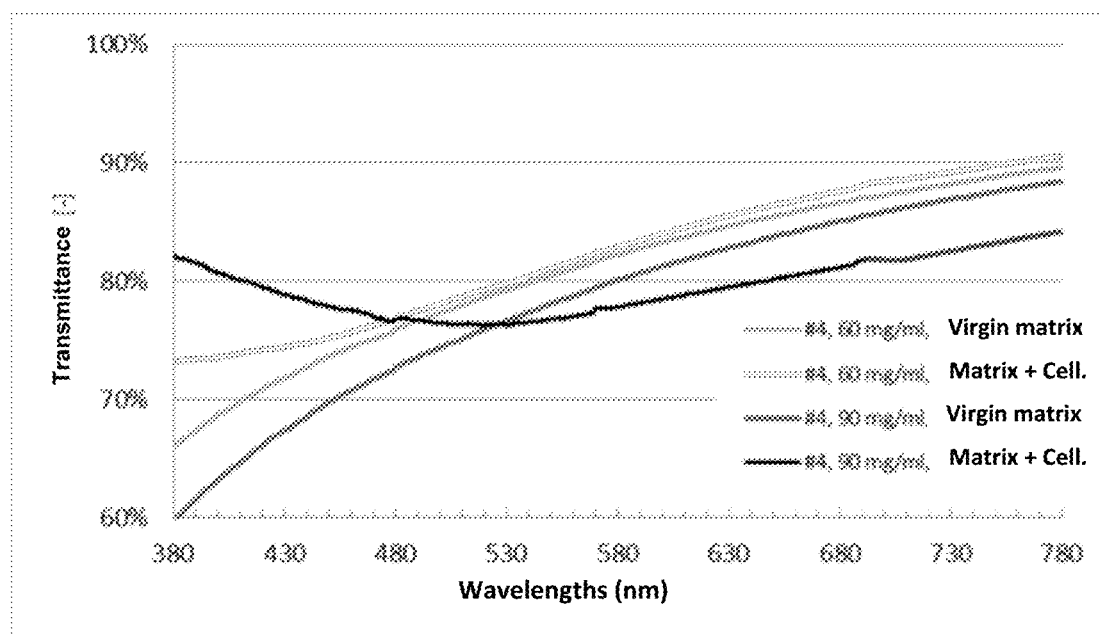

FIG. 10 represents the transparency of the collagen matrices (condition #4, at the collagen concentrations of 60 mg/ml and 90 mg/ml) without and with an epithelium reconstituted in vitro.

Figure 11:
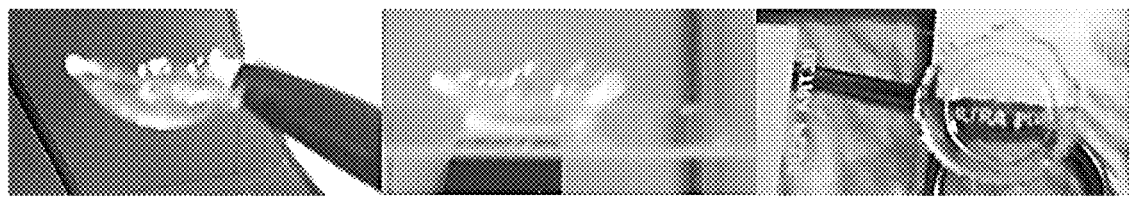

FIG. 11 represents photographs of transparent collagen matrices (condition #4, 60 mg/ml) obtained with the method of the invention, molded so as to mimic a human cornea.

Figure 12:
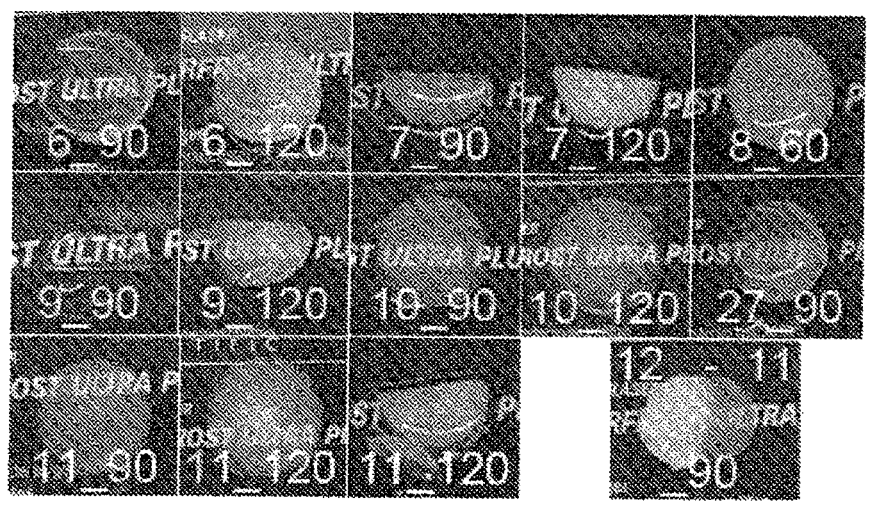

FIG. 12 shows photographs of various matrices molded either with method 1 or with method 2 and according to various concentrations and physicochemical conditions. The text on which the matrices are placed is more or less visible depending on the transparency of the matrix. Photograph 12-11_90 shows a composite matrix.

Figure 13:
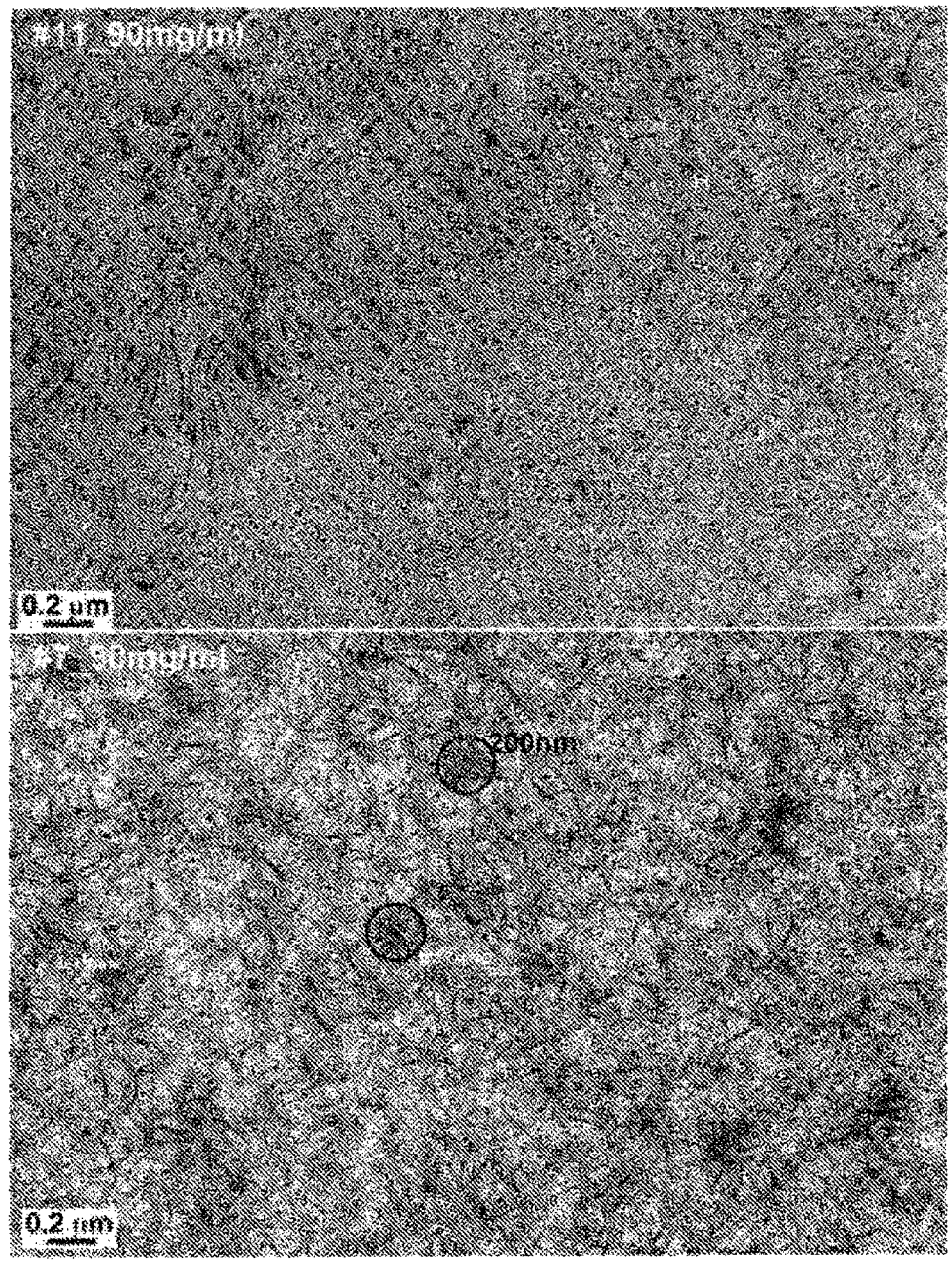

FIG. 13 represents images obtained by transmission electron microscopy of ultrathin sections of matrices synthesized at 90 mg/ml according to the conditions #11 (top) and #7 (bottom). The presence of well individualized and relatively equidistant and organized fibrils is noted at the top (#11), whereas, at the bottom (#7), fibril aggregates 200 nm in diameter, spaced out from one another by crosslinked thin fibrils which impose a relatively regular inter-distance are observed.

Figure 14:
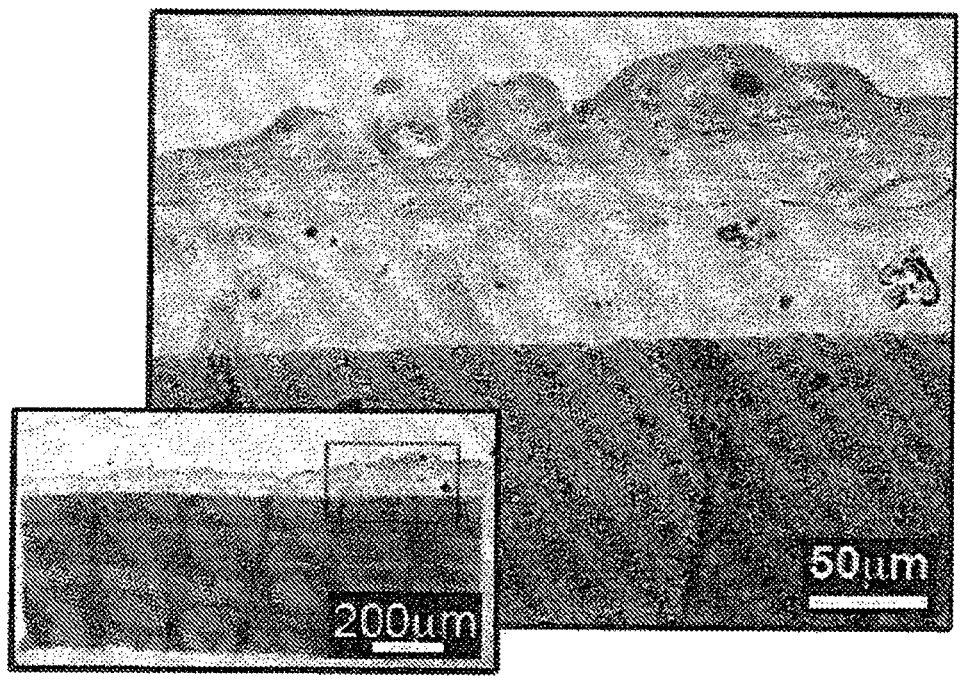

FIG. 14 represents a semi-thin section of a collagen matrix (condition #11, 90 mg/ml) obtained by optical microscopy. At the bottom on the left is a view of the whole and on the right is a zoom of the boxed in zone on the left. The dense matrix and also the layer of epithelial cells which has developed at the surface are observed.

Figure 15:
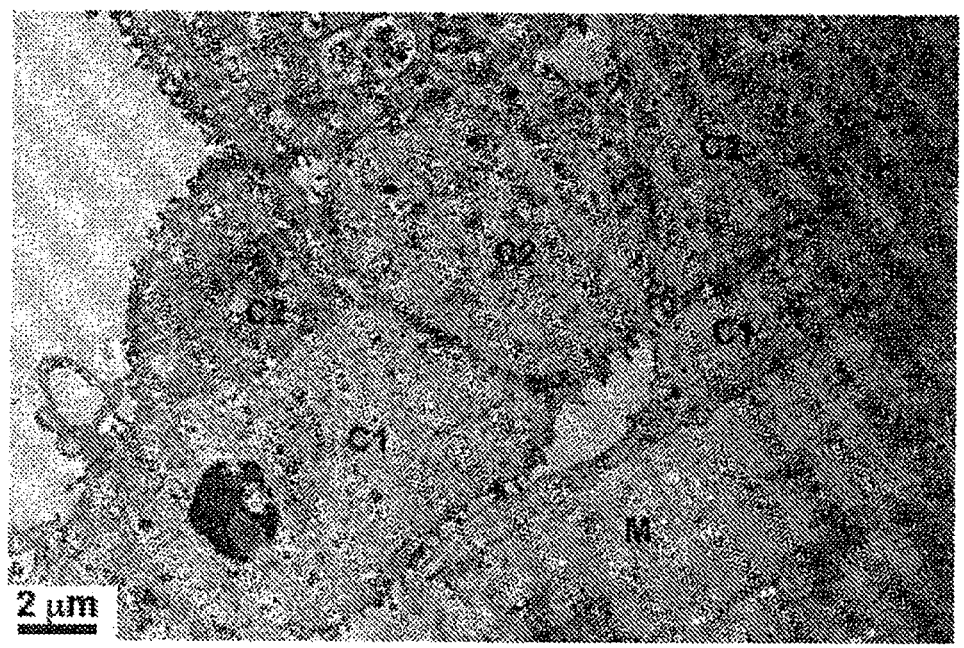

FIG. 15 represents an image obtained by transmission electron microscopy showing the cell layer on a collagen matrix (condition #4, 60 mg/ml). The cells are adherent to the matrix and form an epithelial layer.

Figure 16:
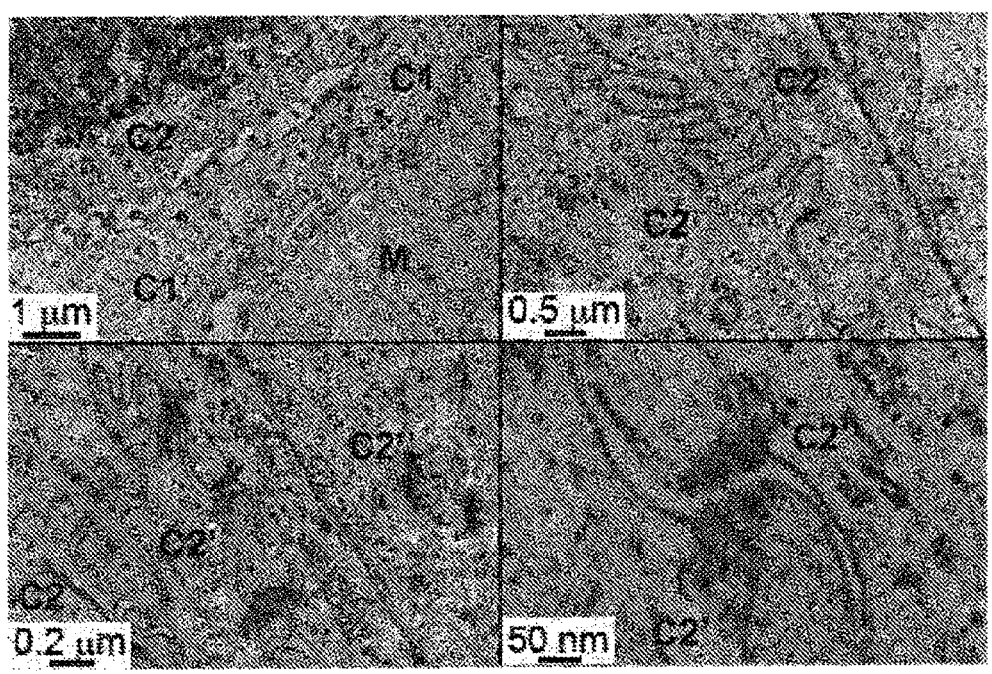

FIG. 16 represents a montage of images obtained by transmission electron microscopy of ultrathin sections of a collagen matrix (condition #11, 90 mg/ml) showing the typical ultrastructures of epithelial cells: top left are the cell stacks on the matrix; top right are the interdigitations between lateral cells; at the bottom are the desmosomes providing adhesion of the cells to one another and the passage of information and nutrients (on the left is a view at low magnification, on the right a zoom on the central desmosome).

Figure 17:
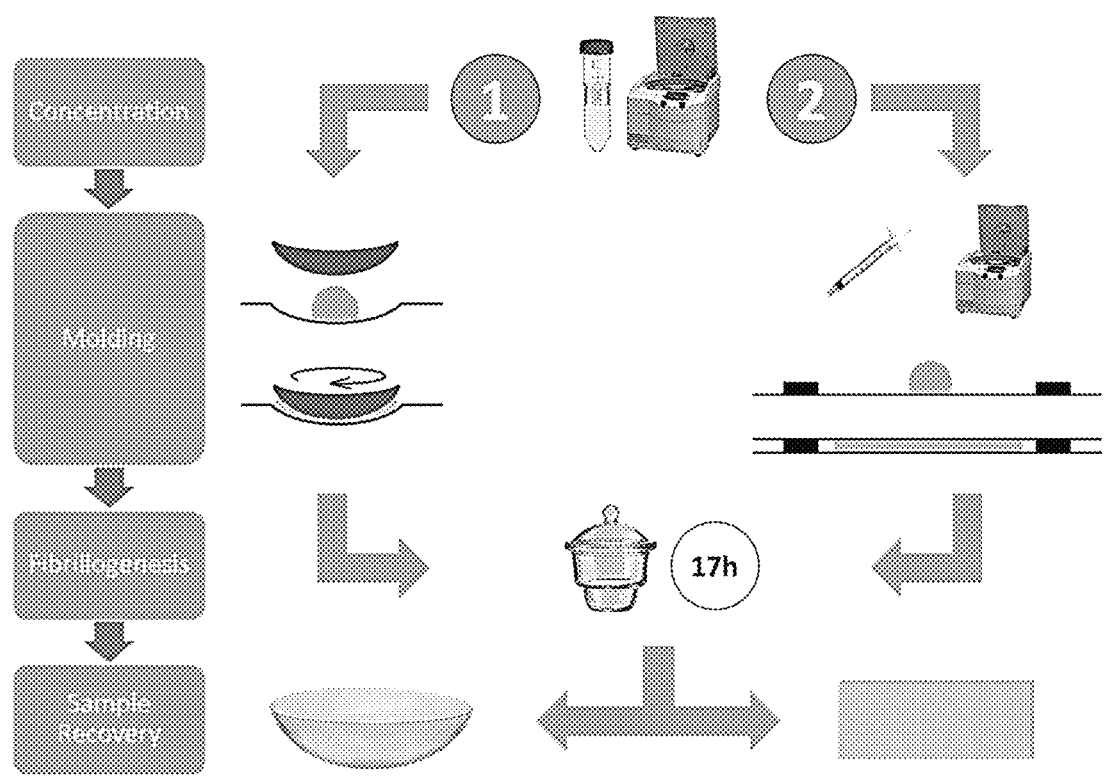

FIG. 17 represents a diagram illustrating the collagen matrix synthesis methods 1 and 2 according to the invention.

Figure 18:
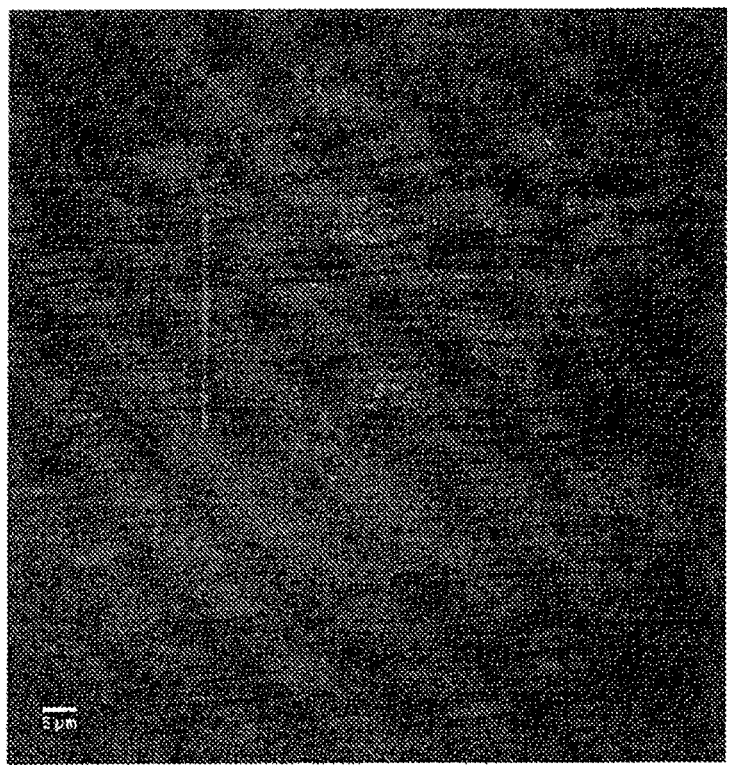
Figure 18:
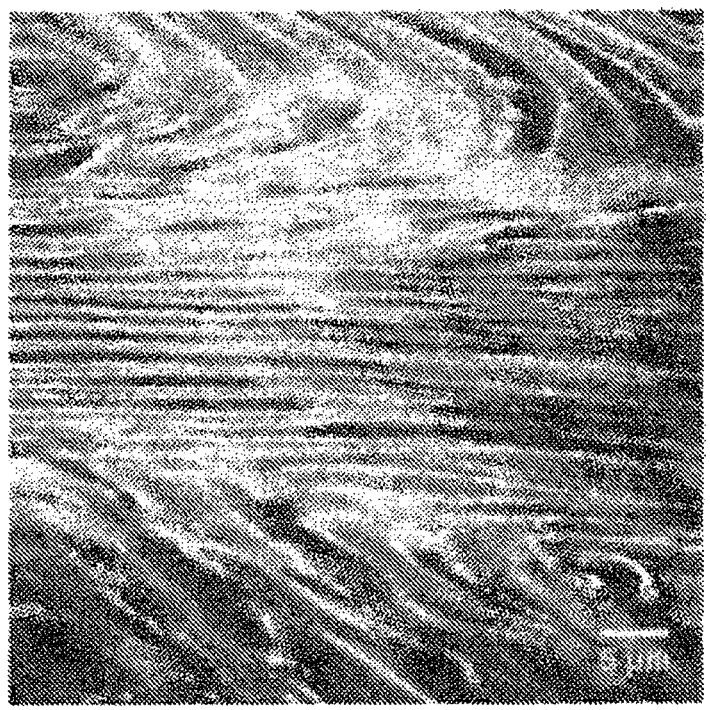

FIG. 18 represents images obtained by second harmonic generation of a collagen solution (condition #36: 0.3 mM HCl and 10 mM $CH_3COOH$) injected into a glass microcell. These images make it possible to verify the type of liquid-crystal organization obtained from the initial physicochemical condition. The intensity profile of these images is typical of that described for a plywood nematic.

FIGS. 19(A)-(C) represent the mechanical strength of the collagen matrices produced under conditions #4 and at various concentrations: (A) Young's modulus expressed in unit Pa; (B) Maximum tensile strength expressed in unit Pa; (C) Maximum elongation at break expressed as % elongation relative to initial length. The Young's modulus and the maximum tensile strength increase with the collagen density, contrary to the elongation at break which, itself, decreases with the collagen concentration. The error bars indicate the standard error of the mean.

Figure 19:
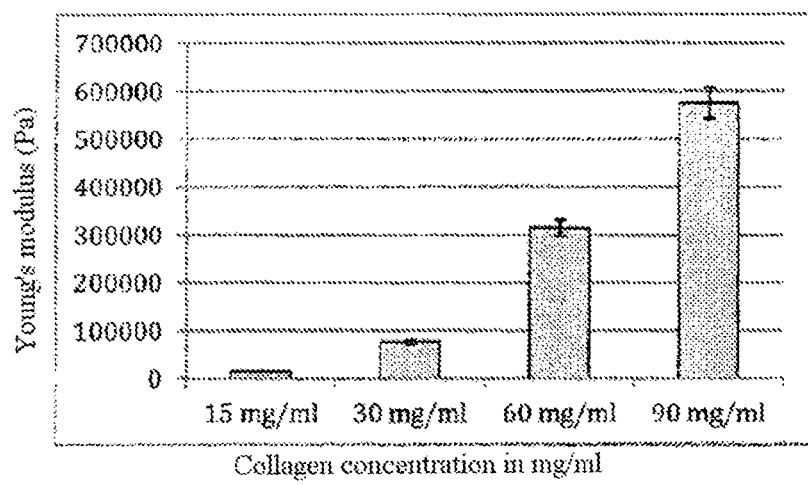
Figure 19:
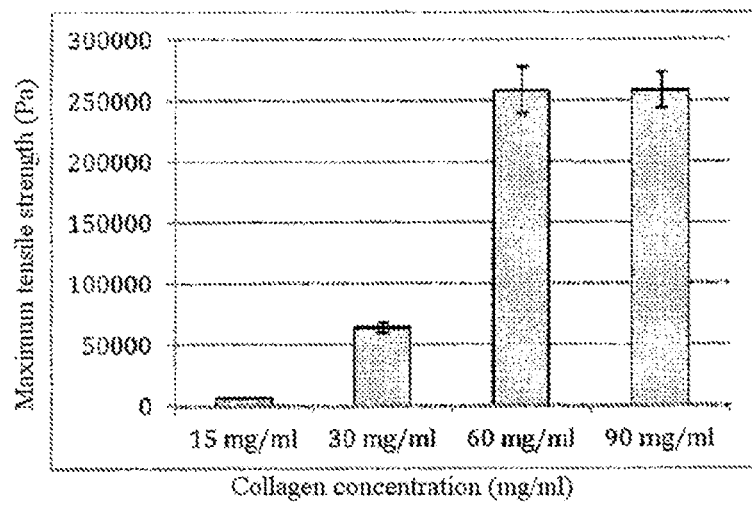
Figure 19:
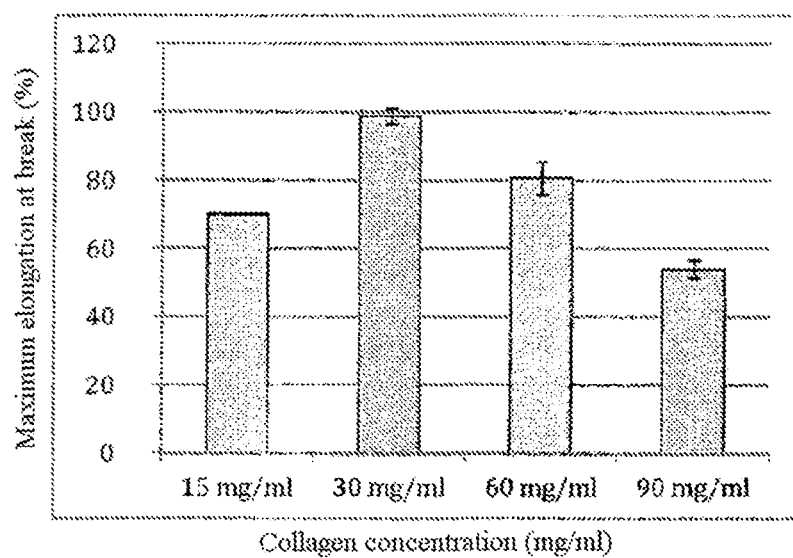

In FIGS. 19 (A)-(C), SEM denotes the Standard Error of the Mean. It is calculated by dividing the standard deviation of the sample by the square root of the number of samples tested ($\sigma/\sqrt{n}$).

FIG. 20 represents the transparency of the fibrillar collagen matrices under conditions #35, #36 and #37 with a collagen concentration of 60 mg/ml.

FIG. 21 represents the transparency of the fibrillar collagen matrices under conditions #36 with a collagen concentration of 90 mg/ml.

Figure 22:
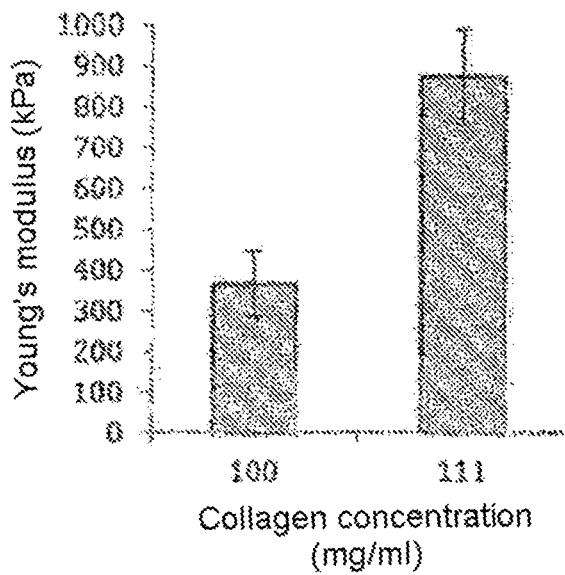
Figure 22:
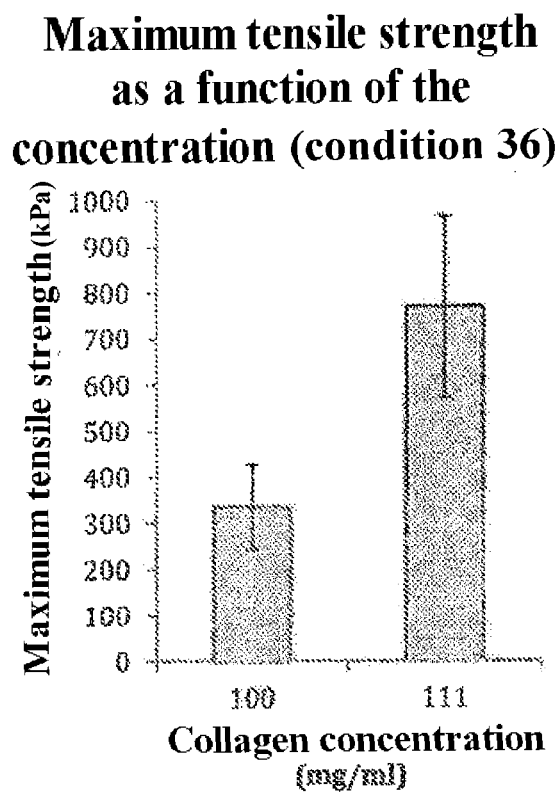
Figure 22:
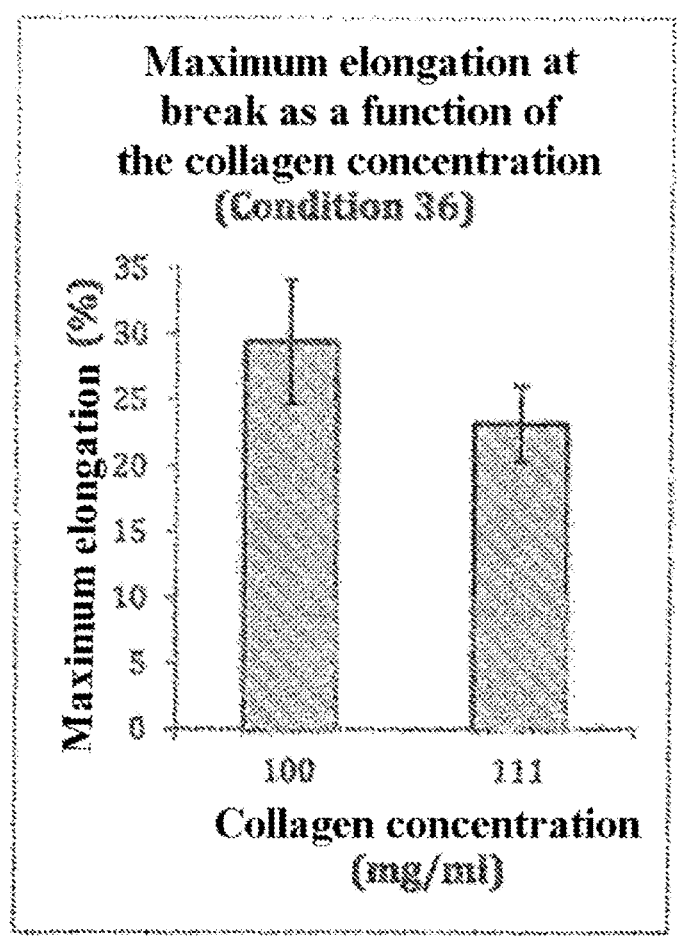

FIGS. 22 (A)-(C) represent the mechanical strength of the collagen matrices produced under conditions #36 and at various concentrations: (A) Young's modulus expressed in unit Pa and kPa; (B) Maximum tensile strength expressed in unit Pa and kPa; (C) Maximum elongation at break expressed as % elongation relative to the initial length. The Young's modulus and the maximum tensile strength increase with the collagen density, contrary to the elongation at break which, itself, decreases with the collagen concentration. The error bars indicate the standard error of the mean. SEM denotes the Standard Error of the Mean. It is calculated by dividing the standard deviation of the sample by the square root of the number of samples tested ($\sigma/\sqrt{n}$).

Figure 23:
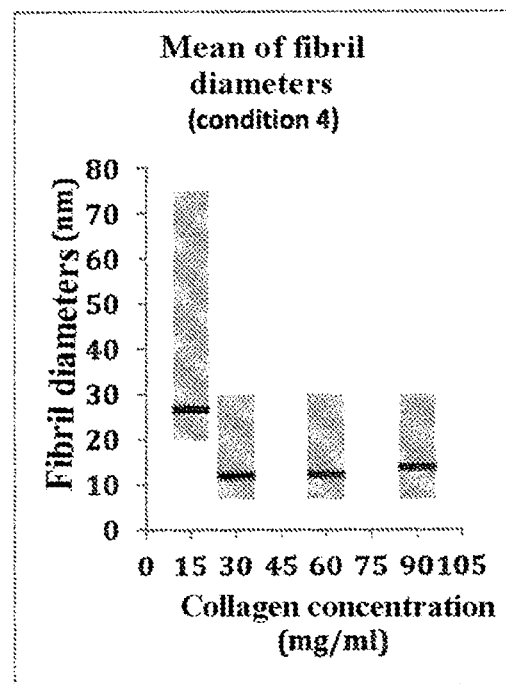

FIG. 23 represents the diameters of the collagen fibrils in the matrices synthesized at various collagen concentrations (15 mg/ml, 30 mg/ml, 60 mg/ml and 90 mg/ml), prepared under the conditions #4. The fibrils in transverse section were detected by processing electron microscopy images using the Image J software. The standard errors and confidence intervals were calculated using the automatic functions of the Microsoft Excel software.

EXAMPLES

The present invention is described in detail by means of the following examples, to which it is not however limited.

In the examples, a collagen type I prepared from tails of young Wistar rats, according to the procedure described by Gobeaux F et al. (Langmuir, 2007, 23, 6411-6417), was used.

The rat tail tendons are excised under a sterile laminar-flow hood, and then washed in a phosphate buffered saline solution containing 137 mM of NaCl, 2.68 mM of KCl, 8.07 mM of $Na_2HPO_4$ and 1.47 mM of $KH_2PO_4$, in order to remove the cells and the traces of blood. The tendons are then soaked in a 4 M NaCl solution in order to remove the remaining intact cells and to precipitate some of the high-molecular-weight proteins. After further washing with the buffered saline solution, and Milli Q water, the tendons are dissolved in an aqueous solution containing 500 mM of acetic acid. The resulting solution is clarified by centrifugation at 4500 rpm (4922 g) for 40 minutes at 10° C., then at 21 000 rpm (53 343 g) for 2 hours at 10° C. A first part of the proteins other than the collagen type I is selectively precipitated from an aqueous 300 mM NaCl solution, then removed by centrifugation at 21 000 rpm (53 343 g) for 2 hours at 10° C. The collagen I is recovered from the supernatant by precipitation from an aqueous 700 mM NaCl solution followed by centrifugation at 4500 rpm (4922 g) for 1 hour at 10° C. The resulting pellets are dissolved in an aqueous 500 mM acetic acid solution, then dialyzed several times against 500 mM acetic acid in order to completely remove the NaCl. The solutions are kept at 4° C. and then centrifuged at 21 000 rpm (53 343 g) for 3 hours at 10° C. The collagen concentration of the acidic solution was determined by hydroxyproline assay. Of course, other collagen sources can be used. A purification can alternatively be carried out by replacing the 500 mM acetic acid with 2.5 mM hydrochloric acid. The collagen solution has a collagen concentration of 3.16 mg/ml and an acetic acid concentration of 500 mM (2.5 mM hydrochloric acid). The pH of the collagen solution is 2.5. The solution is stored in 45 ml sterile tubes at 4° C. The resulting collagen solution is denoted initial collagen solution in the subsequent text.

Example 1

Preparation of the Collagen Solutions for the Synthesis of the Matrices

The inventors put in place an experimental plan in order to determine the effect of acetic acid and of hydrochloric acid and of the respective concentrations thereof on the preparation of collagen matrices.

Extracts of the initial acid-soluble monomeric collagen solution were each dialyzed against solutions comprising hydrochloric acid and/or acetic acid so as to obtain various collagen solutions for the synthesis of matrices. The various collagen solutions used for the synthesis of matrices are described in FIG. 1.

Thus, a certain number of collagen solutions were prepared for the synthesis of matrices. Each collagen solution prepared has a defined concentration of acetic acid and a concentration of hydrochloric acid. These collagen solutions for the synthesis of matrices were concentrated using the filtration-centrifugation technique.

Dialysis of the Initial Collagen Solutions

The initial collagen solution is dialyzed against a solution comprising a mixture of acetic acid and hydrochloric acid. The concentration of acetic acid and of hydrochloric acid of each collagen solution for the synthesis of matrices can be adjusted by repeated cycles of dialysis. A 30 kDa dialysis membrane is used. The dialysis is carried out for approximately 12 hours. A pH measurement is carried out in order to confirm that the dialysis cycle has enabled the desired solution to be obtained.

Concentration of the Dialyzed Collagen Solutions by the Filtration-centrifugation Technique The dialyzed solutions are placed in 20 ml concentrators (Vivaspin 30 kD cutoff) before being centrifuged at low speed on a Beckman-Coulter J26-XP centrifuge (4500 rpm -4922 g, 10° C.) at variable angle. At the end of the concentrating process, the medium collected in the bottom part of the tube is removed so as to avoid rehydration of the concentrated solution.

All the various solutions were thus concentrated to 60 mg/ml of collagen and some, in particular those of conditions #9, #10, #11 and #36, were also concentrated to 90, 100, 110 and 120 mg/ml of collagen. The resulting collagen solutions are stored at 4° C.

The concentrating step makes it possible to have, before fibrillogenesis, a collagen in liquid-crystal form with an ordered and hierarchical organization of the collagen molecules. For example, it was observed that, at the end of the concentrating step, the concentrated solutions (60-80 mg/ml ≤) of the conditions #4, #9, #10 and #11 have a liquid-crystal organization of the cholesteric type, whereas those of the conditions #34, #35, #36, #37 and #38 (45-80 mg/ml ≤) have a nematic-plywood organization. The type of liquid-crystal organization obtained for the various collagen samples before fibrillogenesis can be determined, in particular by photon microscopy between crossed polarizers and by the technique of optical microscopy by second harmonic generation.

FIG. 18 clearly shows a plywood organization of a collagen matrix (condition #36).

Example 2

Preparation of the Fibrillar Collagen Matrices

Molding of the Concentrated Collagen Solutions

The concentrated collagen solutions are placed either in a curved ceramic mold which is pressed with a plastic counterpart (method 1), or in a mold consisting of two flat glass plates kept apart by spacers of defined thickness (method 2) (FIG. 17). Method 1 shows the possibility of obtaining a matrix mimicking the shape of a cornea (FIG. 11).

Fibrillogenesis of Concentrated Collagen Solutions

The fibrillogenesis is induced by exposing the concentrated collagen solutions (optionally placed in a mold) under saturating ammonia vapor (37%) in a closed chamber (3 l) at 20° C. for 7 to 48 hours. A fibrillar collagen matrix is obtained. The collagen matrices can optionally be removed from the mold.

Maturing of the Collagen Matrices

Optionally, the collagen matrices removed from the mold are immersed in demineralized water. The matrices are then left in the water at 20° C. or 4° C. for one month. This step can promote longitudinal growth of the collagen fibrils and stabilization of the collagen matrices. The matrices can then be stored at 4° C. before use (cell culture or implantation in vivo).

Example 3

Transparency of the Fibrillar Collagen Matrices

Figure 2:
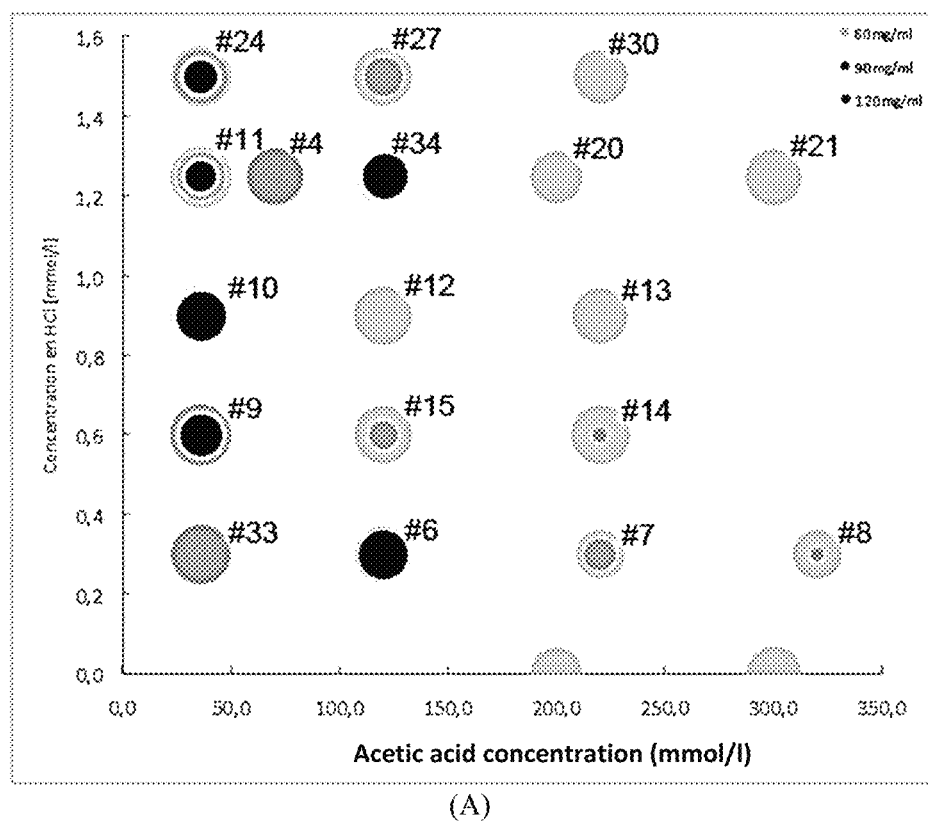
Figure 2:
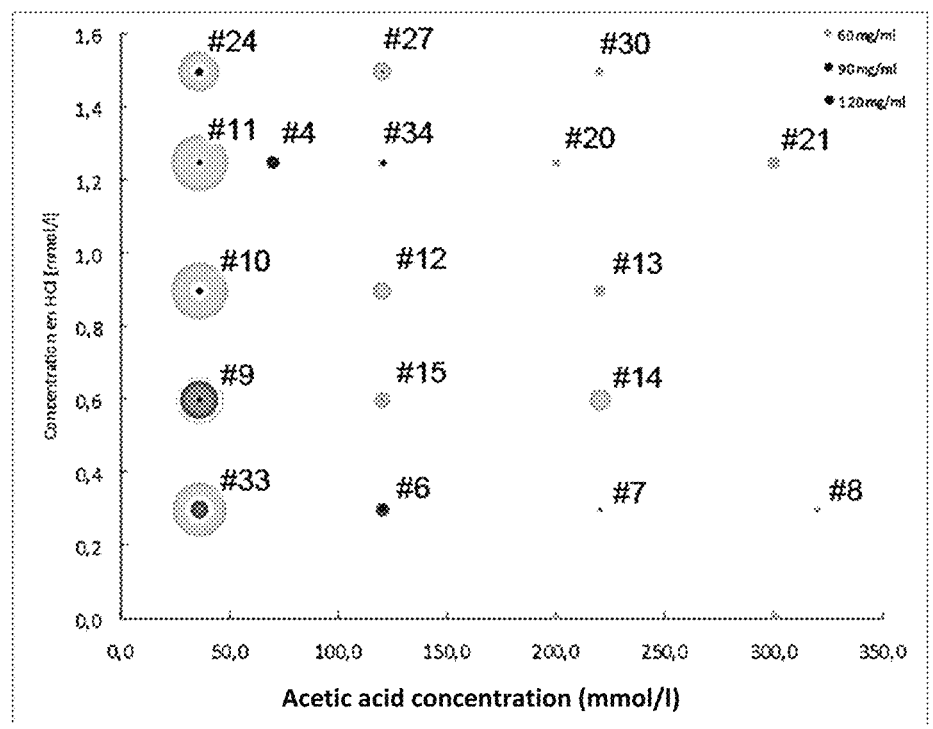

The Transparency Depends on the Physicochemical State During the Fibrillogenesis Various different physicochemical conditions were evaluated in order to optimize the parameters for the synthesis of a transparent collagen matrix. In a first step, the matrices were produced with a collagen concentration of 60 mg/ml, according to procedure 1. Under the conditions #9, #10 and #11, collagen matrices were obtained with collagen concentrations of 90 mg/ml and 120 mg/ml. Collagen matrices were also obtained with a collagen concentration of 90 mg/ml under the conditions #36. The results show that transparent collagen matrices are obtained for some of the conditions tested (FIG. 2A). When the inverse of the absorption coefficient (l/αc) is considered, it is noted that a sample group characterized by relatively low acetic acid concentrations stands out (FIG. 2B). The conditions #9-#11, #34-#38 make it possible to obtain the highest transparency and were therefore studied more particularly.

FIGS. 2, 3, 20 and 21 show the results of transparency of a collagen matrix obtained under these conditions.

Effect of Collagen Concentration on the Transparency of the Collagen Matrices

Figure 3:
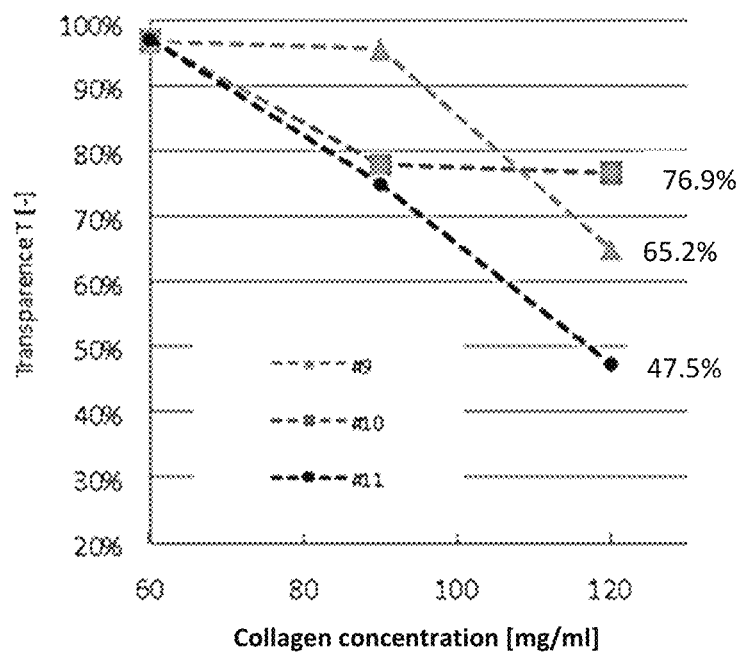
Figure 3:
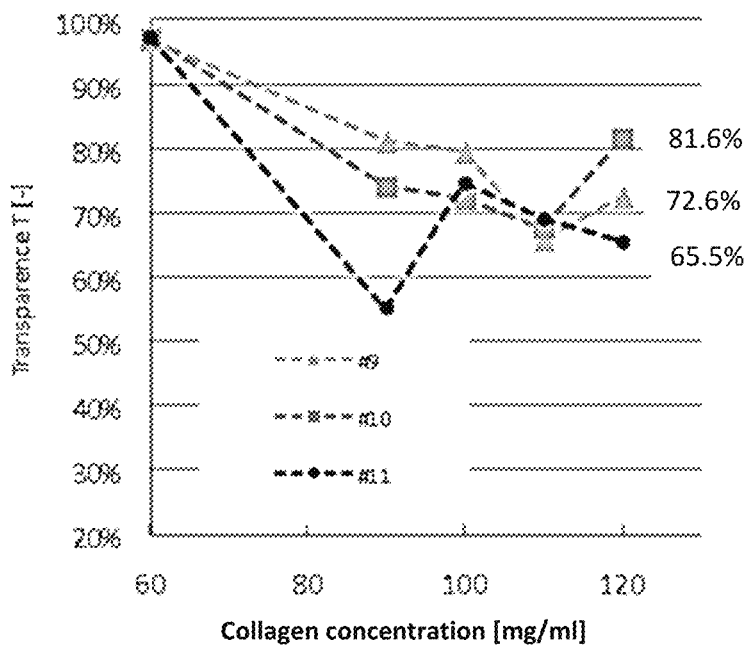

Generally, the higher the collagen concentration, the lower the transparency of the matrix obtained. However, it appears that the decrease in transparency depends on the specific physicochemical conditions during the fibrillogenesis. This effect is illustrated by FIG. 3. For the three conditions #9, #10 and #11, an additional series of samples was produced at various collagen concentrations, ranging from 90 mg/ml to 120 mg/ml, in steps of 10 mg/ml (see FIG. 3B).

The collagen matrices obtained according to procedure 2 come from the same series (spacers of approximately 500 μm). The collagen matrices are therefore supposed to have the same thickness. Consequently, the optical density of the matrix was not adjusted to the thickness of the sample in order to avoid the uncertainty of an additional measurement. The wavelength was limited to the range of 530 nm to 580 nm for reasons of experimental convenience.

Regardless of the protocol, the general trend of a decrease in the transparency of the collagen matrices with an increase in the collagen concentration could be experimentally reproduced, in particular with the condition #9.

Refractive Index of the Collagen Matrices

The refractive indices at 580 nm of bare collagen matrices or collagen matrices having an epithelial layer developed from human limbal explants were measured. The cell-free collagen matrices have a refractive index of 1.333 (FIG. 8A). The collagen matrices with epithelial cells have a refractive index of 1.337 (FIG. 8B). This suggests that the collagen matrices synthesized under a condition which gives rise to a cholesteric and in the absence of the relaxing step prior to the fibrillogenesis step, having or not having an epithelium, do not induce significant light refraction (FIG. 8).

Example 4

Reproducibility of the Collagen Matrices and Variance of the Results

Figures 4, 5:
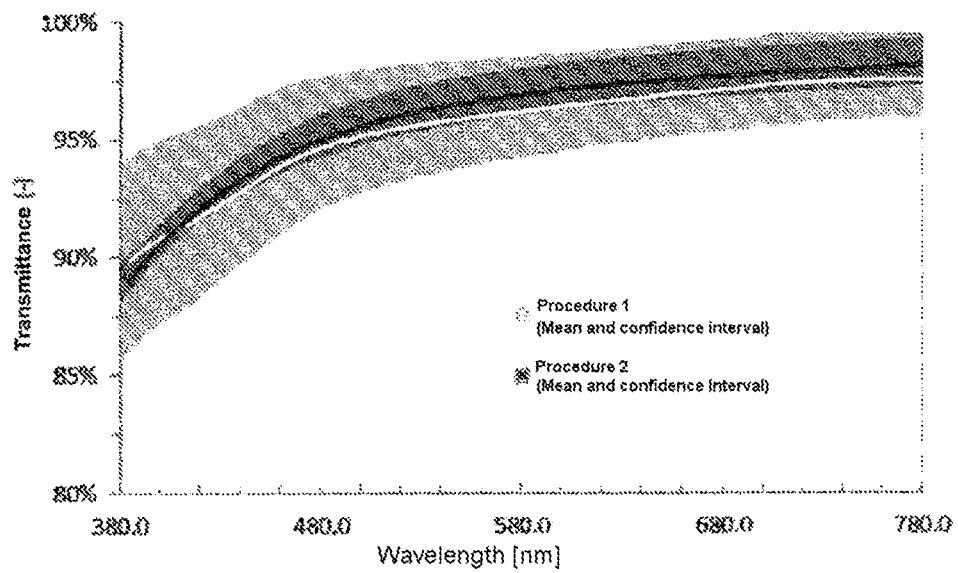
FIG. 5 represents the transparency of the collagen matrices obtained according to procedures 1 and 2, with the condition #11 at 60 mg/ml.

The objective of the modifications that were introduced into the production protocol is to increase the reproducibility of the measurements in order to be able to make a better evaluation of the best synthesis conditions. The use of a flat mold with spacer makes it possible to reduce the variance between the samples with the same physicochemical conditions. This is illustrated by the transparency of the collagen matrices for the condition #11 at 60 mg/ml (FIG. 4). Four samples were prepared for each of the two different production procedures. These two series gave a mean transparency of approximately 96%, but a considerable decrease in the confidence interval 2σ could be obtained with procedure 2 (relative decrease of 83%, see FIG. 5). This suggests that procedure 2 allows a satisfactory reproducibility of the results, thereby allowing the quantification of the macroscopic properties such as transparency of the matrices by taking measurements on three or five samples of the same type.

Example 5

Figure 6:
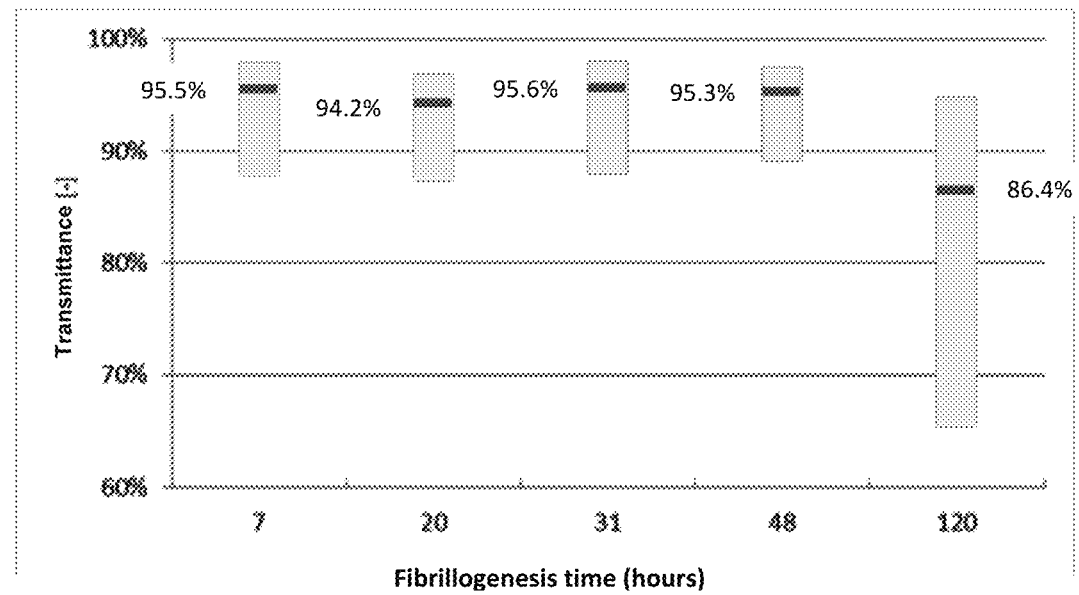
FIG. 6 represents the transparency of the collagen matrices with the condition #11 at 60 mg/ml and at various times of exposure to ammonia vapors. The shaded bands represent the transparency between 380 nm and 780 nm, the mean of the transparency is indicated by the black line.

Effect of Prolonged Exposure to Ammonia Vapors on the Transparency of the Collagen Matrices The samples are left under ammonia vapor for 17 hours in order to induce fibrillogenesis. A set of collagen matrices obtained under condition #11 at 60 mg/ml was exposed to ammonia vapor for different times. It is observed that, when the collagen matrices undergo prolonged exposure of about 120 hours, their transparency significantly decreases (FIG. 6). No notable modification is, on the other hand, observed up to 48 hours of impregnation.

Example 6

Maturation of the Matrices over Time

For all the samples, a change in transparency was observed over time. Generally, the transparency increases over the course of the first two to three weeks, before reaching a threshold value. The specific gain in transparency depends on the physicochemical condition during fibrillogenesis (FIG. 7). For certain conditions, the gain is about 1%, for others it reached levels ranging up to 32%.

Example 7

Mechanical Properties of the Collagen Matrices

There is a direct relationship between the mechanical properties of the collagen matrices and their collagen density.

This relationship was observed for the rigidity, represented by the Young's modulus (FIG. 9A), and also for the maximum mechanical stress supported by the collagen matrices, represented by the maximum tensile strength (FIG. 9B).

This direct relationship between the mechanical properties of the collagen matrices and their collagen density was also observed for the rigidity of collagen matrices at various collagen concentrations (15 mg/ml, 30 mg/ml, 60 mg/ml and 90 mg/ml), prepared under the conditions #4. FIGS. 19 (A)-(C) represent, for these collagen matrices, the Young's modulus or (longitudinal) elastic modulus expressed in unit Pa; the maximum mechanical stress supported by these matrices, represented by the tensile strength expressed in unit Pa; and the capacity of these matrices to elongate before breaking when they are subjected to a tensile strain, expressed as %.

The direct relationship between the mechanical properties of the collagen matrices and their collagen density was also observed for the rigidity of collagen matrices at various collagen concentrations (100 mg/ml and 111 mg/ml), prepared under the conditions #36. FIGS. 22 (A)-(C) represent, for these collagen matrices, the Young's modulus or (longitudinal) elastic modulus expressed in unit Pa and kPa; the maximum mechanical stress supported by these matrices, represented by the tensile strength expressed in unit Pa and kPa; and the capacity of these matrices to elongate before breaking when they are subjected to a tensile strain, expressed as %.

Example 8

Diameter of the Collagen Fibrils in the Matrices Synthesized

The diameters of the collagen fibrils in the matrices synthesized at various collagen concentrations (15 mg/ml, 30 mg/ml, 60 mg/ml and 90 mg/ml), prepared under the conditions #4, were measured (FIG. 23). The fibrils in transverse section were automatically detected by processing electron microscopy images using the Image J software. This processing requires an arbitrary threshold, an area interval and also an elongation factor to be set. A mask is then generated with all the densities automatically selected by the program. This mask is compared with the starting image in order to verify that the densities automatically selected indeed correspond overall to transverse sections of fibril. The standard errors and confidence intervals were calculated using the automatic functions of the Microsoft Excel software (2008). The mean diameter of the fibrils at 15 mg/ml is larger than that of the fibrils at the higher concentrations. It was noted that, despite the increase in the collagen concentration from 30 to 90 mg/ml, the fibril diameter remains comparable.

Example 9

Culturing of Limbal Explants on the Collagen Matrices and Effects on the Transparency Thereof In order to estimate the development of epithelial cells on the collagen matrices, collagen matrices of the condition #4 (condition 60 mg/ml, 90 mg/ml) were washed with pure water (Milli Q) and then with culture medium. Human limbal explants were stitched to the collagen matrices in order to allow cell migration. Such matrices were immersed in a culture medium for 14 days. The cultures were then continued for 10 days, the anterior face of the collagen matrices being left in the open air, thus allowing the generation of an epithelium. Finally, the collagen matrices were used for subsequent observations.

Microscopic observation of the cell cultures makes it possible to show that the epithelial cells are viable and proliferate on the collagen matrices. The cells migrate from the natural explant and extend so as to colonize the surface of the collagen matrices (FIGS. 14 and 15). The ultrastructures characteristic of epithelial cells are clearly observed by transmission electron microscopy (FIG. 16).

The transparency of the collagen matrices was measured before the beginning of the cell culture and then after 24 days. The results show that the transparency of the matrix is affected little by the cell colonization (FIG. 10).

Example 10

Synthesis of Composite Matrices

Solutions from different physicochemical conditions can be placed side by side of one another so as to form composite matrices (FIG. 12).

The invention claimed is:

1. A method for preparing a transparent, dense, fibrillar collagen matrix, comprising the following steps:
   (a) preparing an acidic aqueous solution comprising
       collagen in the form of monomers at a concentration of between 0.1 and 10 mg/ml, and
       at least one strong acid present at a concentration of from 0.2 to 2.5 mM and one weak acid present at a concentration of between 2 and 125 mM;
   (b) concentrating the solution obtained in (a) to a collagen concentration of between 40 and 120 mg/ml;
   (c) forming the fibrils by treating the collagen solution obtained in step (b) with a basic gas phase or basic liquid phase,
   wherein the density of the transparent, dense, fibrillar collagen matrix is greater than or equal to 40 mg/ml, and
   wherein the at least one weak acid is selected from the group consisting of acetic acid, chloroacetic acid, dichloroacetic acid, trichloroacetic acid, bromoacetic acid, trifluoroacetic acid, propionic acid, ascorbic acid, valeric acid, 2-bromovaleric acid, 4-bromovaleric acid, 5-bromovaleric acid, lactic acid, citric acid, salicylic acid, acetylsalicylic acid, formic acid, and acids of the uronic acid family, and
   the at least one strong acid is selected from the group consisting of hydrochloric acid, sulfuric acid, perchloric acid, hydrofluoric acid, hydriodic acid, chloric acid, permanganic acid, and manganic acid.

2. The method as claimed in claim 1, wherein the strong acid is hydrochloric acid and the weak acid is acetic acid.

3. The method as claimed in claim 1, wherein, in step (b), the concentrating of the solution is carried out by filtration-centrifugation, by ultrafiltration, by rapid evaporation under cryo-centrifugation or by reverse osmosis.

4. The method as claimed in claim 1, further comprising, after the concentrating step (b) and before the step of forming the fibrils (c), a step of shaping the collagen solution and/or a relaxing step.

5. The method as claimed in claim 4, wherein the shaping step is a molding step.

6. The method as claimed in claim 1, wherein, in step (c), the treatment with a basic gas phase is a treatment with ammonia vapor.

7. The method as claimed in claim 1, further comprising, after the step of forming the fibrils (c), a maturing step.

8. The method for preparing a transparent, dense, fibrillar collagen matrix as claimed in claim 1, comprising the following steps:
   (a) preparing an acidic aqueous solution comprising:
   collagen in the form of monomers at a concentration of between 0.1 and 10 mg/ml, and
   acetic acid at a concentration of between 2 and 125 mM and hydrochloric acid present at a concentration of from 0.2 to 2.5 mM;
   (b) concentrating the solution obtained in (a) by filtration-centrifugation to a collagen concentration of between 40 and 120 mg/ml;
   shaping the collagen solution obtained in the concentrating step;
   relaxing the collagen solution at the end of the shaping step;
   (c) forming the fibrils by treating the collagen solution obtained in the relaxing step with a basic gas phase consisting of ammonia vapors; and
   (d) maturing the fibrils obtained in step (c) until a transparent matrix is obtained,
   wherein the density of the transparent, dense, fibrillar collagen matrix is greater than or equal to 40 mg/ml.

9. A transparent fibrillar collagen matrix obtained by the method as claimed in claim 1, wherein the transparent fibrillar collagen matrix transmits at least 80% of white light and wherein the transparent fibrillar collagen matrix has a collagen density greater than or equal to 40 mg/ml.

10. A composite fibrillar collagen matrix obtained by the method as claimed in claim 1, wherein the composite fibrillar collagen matrix comprises at least one opaque zone which transmits less than 80% of white light and at least one zone which transmits at least 80% of white light.

11. An artificial tissue or organ, comprising the transparent fibrillar collagen matrix of claim 9.

12. The artificial tissue or organ of claim 11, wherein the tissue is a cornea substitute.

13. An artificial tissue or organ, comprising the composite fibrillar collagen matrix of claim 10.

14. The artificial tissue or organ of claim 13, wherein the tissue is a cornea substitute.

* * * * *